(12) United States Patent
Sandvang et al.

(10) Patent No.: US 12,364,719 B2
(45) Date of Patent: *Jul. 22, 2025

(54) BACILLUS SUBTILIS STRAINS IMPROVING ANIMAL PERFORMANCE PARAMETERS

(71) Applicant: CHR. HANSEN A/S, Hoersholm (DK)

(72) Inventors: Dorthe Sandvang, Slangerup (DK); Tina Styrishave, Ringsted (DK)

(73) Assignee: CHR. HANSEN A/S, Hoersholm (DK)

( * ) Notice: Subject to any disclaimer, the term of this patent is extended or adjusted under 35 U.S.C. 154(b) by 505 days.

This patent is subject to a terminal disclaimer.

(21) Appl. No.: 17/709,277

(22) Filed: Mar. 30, 2022

(65) Prior Publication Data

US 2022/0218763 A1    Jul. 14, 2022

Related U.S. Application Data

(63) Continuation of application No. 16/492,897, filed as application No. PCT/EP2018/056442 on Mar. 14, 2018, now Pat. No. 11,291,695.

(30) Foreign Application Priority Data

Mar. 14, 2017  (EP) ..................................... 17160843
Feb. 2, 2018  (EP) ..................................... 18154862

(51) Int. Cl.
| | |
|---|---|
| *A61K 35/742* | (2015.01) |
| *A01N 63/00* | (2020.01) |
| *A23K 10/18* | (2016.01) |
| *A23K 50/75* | (2016.01) |
| *A61K 9/00* | (2006.01) |
| *C12N 1/20* | (2006.01) |
| *C12R 1/125* | (2006.01) |

(52) U.S. Cl.
CPC ............ *A61K 35/742* (2013.01); *A23K 10/18* (2016.05); *A23K 50/75* (2016.05); *A61K 9/0053* (2013.01); *C12N 1/205* (2021.05); *A01N 63/00* (2013.01); *C12R 2001/125* (2021.05)

(58) Field of Classification Search
CPC ............................ A61K 35/742; A23K 1/1846
See application file for complete search history.

(56) References Cited

U.S. PATENT DOCUMENTS

| | | | |
|---|---|---|---|
| 9,844,573 B2 | 12/2017 | Nielsen et al. | |
| 10,702,560 B2 | 7/2020 | Nielsen et al. | |
| 11,291,695 B2 * | 4/2022 | Sandvang | ............... A61P 31/04 |
| 2012/0128827 A1 | 5/2012 | Ochoa | |

FOREIGN PATENT DOCUMENTS

| | | |
|---|---|---|
| EP | 0 287 699 B1 | 10/1988 |
| WO | WO-2005/019417 | 3/2005 |
| WO | WO-2010/033714 | 3/2010 |
| WO | WO-2012/009712 | 1/2012 |
| WO | WO-2013/153159 | 10/2013 |
| WO | WO-2016/060934 | 4/2016 |
| WO | WO-2016/118840 | 7/2016 |

OTHER PUBLICATIONS

EFSA Panel on Additives and products or substances Used in Animal Feed (EFSA journal, vol. 8, Issue 4, pp. 1-13, 2020) (Year : 2020).*
European Food Safety Authority Journal, "Guidance on the assessment of bacterial susceptibility to antimicrobials of human and veterinary importance", EFSA Journal 2012;10(6):2740.
"Safety and efficacy of GalliPro Fit (Bacillus subtilis DSM 32324, Bacillus subtilis DSM 32325 and Bacillus amyloliquefaciens DSM 25840) for all poultry species for fattening or reared for laying/breeding," EFSA journal, vol. 18, Issue 4: 6094, pp. 1-13, (Mar. 2020).
Alali et al., "Effect of essential oil compound on shedding and colonization of *Salmonella enterica serovar* Heidelberg in broilers", (2013) Poultry Science 92: 836-841.
Barbosa et al., "Screening for *Bacillus* Isolates in the Broiler Gastrointestinal Tract," Applied and Environmental Microbiology, vol. 71, No. 2, pp. 968-978, Feb. 2005.

(Continued)

*Primary Examiner* — Brian Gangle
*Assistant Examiner* — Lakia J Jackson-Tongue
(74) *Attorney, Agent, or Firm* — Adam Rucker

(57) ABSTRACT

The present invention provides a *Bacillus subtilis* strain selected from the group consisting of a) the strain deposited as DSM32324,b) the strain deposited as DSM32325, and c) a mutant strain of (a) or (b) which has sensitivity for ampicillin, vancomycin, gentamicin, kanamycin, streptomycin, erythromycin, clindamycin, tetracycline, and chloramphenicol; and has inhibitory activity against *E. coli* and Clostridium perfringens. The invention further relates to *Bacillus* compositions comprising at least one *Bacillus subtilis* strain of the invention, preferably the *Bacillus subtilis* strain DSM32324 and/or the *Bacillus subtilis* strain DSM32325, as Direct Fed Microbial (DFM), premix, animal feed additive or animal feed. The invention provides a method of improving one or more animal performance parameters selected from the group consisting of i) increased weight gain (WG), ii) lower feed conversion ratio (FCR), iii) lower necrotic enteritis lesion scoring, iv) lower necrotic enteritis frequency, v) lower necrotic enteritis mortality, vi) increased European Production Efficacy Factor (EPEF), and vii) lower mortality, by feeding a strain or a composition according to the invention to an animal.

20 Claims, No Drawings

(56) References Cited

OTHER PUBLICATIONS

Benitez et al., "Antimicrobial Activity of *Bacillus amyloliquefaciens* LBM 5006 is enhanced in the Presence of *Escherichia coli*," Curr Microbiol 62, pp. 1017-1022, Nov. 2010.
Chaiyawan et al., "Characterization and Probiotic Properties of *Bacillus* strains isolated from Broiler," The Thai Journal of Veterinary Medicine, vol. 40, pp. 207-214, 2010.
Cutting, "*Bacillus* probiotics," Food Microbiology, No. 28, pp. 214-220, 2010 (Mar. 2010).
European Food Safety Authority Journal, "Update of the criteria used in the assessment of bacterial resistance to antibiotics of human or veterinary importance," The EFSA Journal, No. 732, pp. 1-15, Jun. 2008.
Guo et al. "Screening of *Bacillus* strains as potential probiotics and subsequent confirmation of the in vivo effectiveness of *Bacillus subtilis* MA139 in pigs," Antonie van Leewenhoek, vol. 90, pp. 139-146, Jul. 2006.
International Search Report dated Jun. 13, 2013 issued in PCT/EP2013/057590.
Johnson et al., "Anticoccidial drugs: Lesion Scoring Techniques in Battery and Floor-pen Experiments with Chickens," Exp Parasitol., Aug. 1970;28(1):30-6.
Klose et al., "In vitro antagonistic activities of animal intestinal strains against swine-associated pathogens," Veterinary Microbiology, No. 144, pp. 515-521, Feb. 2010.
Knap et al., "*Bacillus licheniformis* Prevents Necrotic Enteritis in Broiler Chickens," Avian Diseases, (Jun. 2010) 54(2):931-5.
López and Kolter, "Extracellular signals that define distinct and coexisting cell fates in *Bacillus subtilis*," FEMS Microbiol. Rev., No. 34, pp. 134-149, Dec. 2009.
Spiehs et al., "Effects of two direct-fed microbial on the ability of pigs to resist an infection with *Salmonella enterica* serovar Typhimurium," Journal of Swine Health and Production, vol. 16, No. 1, pp. 27-36, Jan. 2008.
Timbermont et al., "Origin of *Clostridium perfringens* isolates determines the ability to induce necrotic enteritis in broilers," Comparative Immunology Microbiology Infectious Disease, (Nov. 2009); 32(6):503-12.
Waititu et al. "Effect of Supplementing Direct-Fed Microbials on Broiler Performance, Nutrient Digestibilities and Immune Responses," Poultry Science, (2014), 93 (3), 625-635.
Wang et al., "Comparison of gyrB gene sequences, 16S rRNA gene sequences and DNA-20 DNA hybridization in the *Bacillus subtilis* group," Int J Syst Evol Microbiol. (Aug. 2007) 57 (Pt8):1846-50.
Zaghari et al., "Effect of *Bacillus Subtilis* Spore (GalliPro®) Nutrients Equivalency Value on Broiler Chicken Performance," Italian Journal of Animal Science, vol. 14:3555 (2015).

\* cited by examiner

BACILLUS SUBTILIS STRAINS IMPROVING ANIMAL PERFORMANCE PARAMETERS

CROSS-REFERENCE TO RELATED APPLICATIONS

The present application is a continuation of U.S. application Ser. No. 16/492,897, filed Sep. 10, 2019, which is the U.S. National Stage of International Application No. PCT/EP2018/056442, filed Mar. 14, 2018, and claims priority to European Patent Application Nos. 18154862.9, filed Feb. 2, 2018, and 17160843.3, filed Mar. 14, 2017.

FIELD OF THE INVENTION

The present invention provides a *Bacillus subtilis* strain selected from the group consisting of a) the strain deposited as DSM32324, b) the strain deposited as DSM32325, and c) a mutant strain of (a) or (b) which has sensitivity for ampicillin, vancomycin, gentamicin, kanamycin, streptomycin, erythromycin, clindamycin, tetracycline, and chloramphenicol; and has inhibitory activity against *Escherichia coli* and *Clostridium perfringens*.

The invention further relates to *Bacillus* compositions comprising at least one *Bacillus subtilis* strain of the invention, preferably the *Bacillus subtilis* strain DSM32324 and/or the *Bacillus subtilis* strain DSM32325, as Direct Fed Microbial (DFM), premix, animal feed additive or animal feed.

The invention provides a method of improving one or more animal performance parameters selected from the group consisting of i) increased weight gain (WG), ii) lower feed conversion ratio (FCR), iii) lower necrotic enteritis lesion scoring, iv) lower necrotic enteritis frequency, v) lower necrotic enteritis mortality, vi) increased European Production Efficacy Factor (EPEF), and vii) lower mortality, by feeding a strain or a composition according to the invention to an animal.

BACKGROUND OF THE INVENTION

The phase-out of antibiotic growth promoters in the European Union in 2006 has resulted in an increased need for cost-effective feed additives with high efficacy and susceptibility to inhibitorys of human and veterinary importance.

*Bacillus*-based probiotic feed additives are known for their positive effects on health and production in pigs and poultry. These products are relevant for the feed industry because spores are heat stable and can survive the pelletizing process at temperatures up to 90-95° C. The endospore-forming bacteria *Bacillus subtilis* and *Bacillus licheniformis* are Generally Regarded as Safe (GRAS) by the U.S. Food and Drug Administration (FDA) and acceptable for inclusion in an animal diet or water by the Association of American Feed Control Officials (AAFCO).

WO2013/153159 describes a method for selecting a *Bacillus* strain having antibiotic sensitivity, inhibitory activity against *E.coli* and *Clostridium perfringens*, and high sporulation.

Many of the isolates screened showed undesirable antibiotic resistance above breakpoints defined by the European Food Safety Authority (EFSA) and were discarded due to safety concerns. Several of the isolates showed inhibition of *Clostridium perfringens* while only a few isolates inhibited *E. coli*. The strains with the best inhibition of pathogens were primarily of the species *B. amyloliquefaciens*.

WO2016/060934 shows in Table 7 the anti-*E. coli* activity of 10 *Bacillus* strains. Five of the six *B. amyloliquefaciens* strains demonstrate anti-*E. coli* activity while only one of the two *B. subtilis* strains, the strain isolated from Kemin product, clostat, demonstrated anti-*E. coli* activity. Interestingly, this strain has later been found to be a *B. amyloliquefaciens* cf. WO2016/118840 (page 46, line 23).

WO2016118840 describes various *Bacillus* strains for improving health and performance of production animals, in particular two B. *amyloliquefaciens* strains and two B. *subtilis* strains (see Table 3.1). Only two of the strains, the B. *subtilis* strain deposited as DSM29870 and the B. *amyloliquefaciens* strain deposited as DSM29869, were found to be sensitive for all eight antibiotics tested. Results for ampicillin were not provided.

The *B. subtilis* strain deposited as DSM29870 was found to inhibit growth of *E. coli* strains ATCC10535 and ATC25922 in vitro (Example 4). Example 7 provides the results of three *Clostridium perfringens* challenge trials. There was no significant difference between the DSM29870 fed group (T4) and the bacitracin fed group (T3) with regards to all parameters measured in these trials. Results for BWG, FCR and bird mortality with Necrotic enteritis lesions were intermediate between the non-infected, non-treated group (T1) and the infected, non-treated group (T2).

However, there is still a need for probiotic strains which can be used for improving health and performance of production animals.

SUMMARY OF THE INVENTION

The present invention provides a *Bacillus subtilis* strain selected from the group consisting of a) the strain deposited as DSM32324, b) the strain deposited as DSM32325, and c) a mutant strain of (a) or (b) which has sensitivity for ampicillin, vancomycin, gentamicin, kanamycin, streptomycin, erythromycin, clindamycin, tetracycline, and chloramphenicol; and has inhibitory activity against *E. coli* and *Clostridium perfringens*.

A bacterial strain refers to a bacterium which remains genetically unchanged when grown or multiplied. The multiplicity of such identical bacteria is included when reference is made to a strain.

Compositions comprising at least one *Bacillus subtilis* strain according to the invention, e.g. as Direct Fed Microbial (DFM), an animal feed additive or premix, or an animal feed may be fed to an animal.

At least one *Bacillus subtilis* strain according to the invention may be added to the feed during production, after production by the supplier or by the person feeding the animal, just prior to providing the feed to the animal. The *Bacillus subtilis* bacteria used in the methods and compositions described herein are particularly suitable because they are capable of surviving (as spores) the heat and pressure conditions of the process of producing a dry pelleted feed product.

Necrotic enteritis caused by *Clostridium perfringens* has become a grave economic problem in modern poultry production. The purpose of some of the in vivo studies described in the examples was to investigate the effect of feed additives comprising a *Bacillus subtilis* strain according to the invention on the pathogenesis of necrotic enteritis (NE) in broiler cage studies. Other in vivo studies in poultry focused on performance with or without challenge with *Clostridium perfringens*.

Individual battery/floor pen studies have been performed to evaluate the influence of *Bacillus subtilis* DSM32324 and DSM32325 on the development of subclinical necrotic enteritis. Two different independent research facilities have been used, one based in Europe (Example 3, DSM32324) and the other in the United States (Example 4, DSM32325) meaning that slightly different evaluation parameters were used to assess the effect of the two strains.

For *Bacillus subtilis* DSM3234 the performance parameters feed conversion rate (FCR) and average weight gain (AWG) measured at day 21, day 35 and day 42 showed a significant improvement for all data points when considering *Bacillus subtilis* DSM3234 as a feed additive compared to the untreated infected control group. Surprisingly, the *Bacillus* treated group did not show any significant differences to the not-infected, non-medicated control group, even though the latter group did not receive the challenge and was considered healthy (Table 7).

In the induced subclinical enteritis challenge in vivo trial the *Bacillus subtilis* DSM3234 decreased necrotic enteritis lesion scoring in chicken and reduced necrotic enteritis mortality significantly (Table 8).

The *Bacillus subtilis* DSM32325 decreased necrotic enteritis frequency in chicken compared to infected untreated control in a statistically significant manner when the data of Day 25 and 26 were combined. Surprisingly, the necrotic enteritis frequency was even lower in the *Bacillus* treated group than in the Amoxicilin treated control group (Table 9).

Further, *Bacillus subtilis* DSM32325 reduced necrotic enteritis severity (mean score) compared to infected untreated control in a statistically significant manner when the data of Day 25 and 26 were combined. Surprisingly, the mean score was even lower in the *Bacillus* treated group than in the Amoxicilin treated group (Table 10).

The two *B. subtilis* strains have also been evaluated in two performance feeding trials, Example 5 (DSM32324 and DSM32325) and Example 6 (DSM32324).

Example 5 provides the results of a trial of 1800 Ross 308 male broilers and found that for the global fattening period (0-42 days of age), broilers supplemented with the Bacilli strains DSM32324 or DSM32325 grew significantly more than control animals. The feed conversion (FCR) and EPEF of all broilers supplemented with DSM19489, DSM32324 and DSM32325 were significantly improved when compared to those of the control animals.

Example 6 provides the results of a trial of 1300 Ross 308 male broilers per treatment group and demonstrates that DSM19489 had a tendency of reduced mortality (p=0.096) and *Bacillus subtilis* DSM32324 a marked and significantly reduced mortality in especially the finisher period which also served for statistical significance of mortality for the overall trial.

Example 7 investigates the effect of three selected Bacilli strains (DSM32324, DSM32325 and DSM25840) on performance and apparent ileal digestibility and concluded that all three strains showed surprisingly good and significantly improved results.

Birds supplemented with DSM32324 showed a higher daily weight gain (Table 16), daily feed intake and feed conversion ratio in the starter period (data not shown) and a higher protein digestibility at D42 (Table 17) compared to non-supplemented birds.

Birds supplemented with DSM25840 showed a higher daily weight gain (Table 16) and daily feed intake in the starter period (data not shown), a higher body weight at D42 (Table 16) and a higher ash, protein and energy digestibility at D42 (Table 17) compared to non-supplemented birds.

Birds supplemented with DSM32325 showed a higher daily weight gain (Table 16) and daily feed intake in the starter period (data not shown), and a lower Ca and Phosphorus digestibility at D42 (Table 17) compared to non-supplemented birds.

In conclusion, these studies have demonstrated that the *Bacillus subtilis* strains deposited as DSM32324 and DSM32325 show effect on reduction of necrotic enteritis in in vivo challenge trials and positive effect on performance parameters in poultry. Important findings were significant increase of Weight Gain (WG), significant decrease of Feed Conversion Ratio (FCR), significant decrease of mortality and significant increase of European Production Efficacy Factor (EPEF).

Example 8 shows that a *Bacillus* composition of the invention, named EPB5, comprising DSM32324, DSM25840 and DSM32325 in a ratio of 8:3:5, improved performance in broilers when compared to birds fed corresponding diets without addition of the probiotic. Positive responses were demonstrated on feed conversion ratio and average weight gain. Surprisingly, EPB5-treated groups showed significant improvement for some of the performance parameters compared to the groups with the *Bacillus* single strain treatment which again showed significant differences in performance parameters to the non-medicated infected control group. Further, both the single strains *Bacillus subtilis* DSM32234, *Bacillus subtilis* DSM32235 and *Bacillus amyloliquefaciens* DSM25840 as well as the combination EPB5 decreased necrotic enteritis lesion scoring in chicken and reduced necrotic enteritis mortality significantly in an in vivo challenge trial.

Example 9 shows that a *Bacillus* composition of the invention improved performance in turkeys from d 1 to d 147 of age (147-d feeding period) at dose levels from 250 mg/kg to 2000 mg/kg when compared to birds fed corresponding diets without addition of the probiotic. Positive responses were demonstrated on body weight gain, feed conversion ratio and dry matter content of excreta.

Example 10 shows that a *Bacillus* composition of the invention can be combined with a vaccine, such as a live *Salmonella* Typhimurium vaccine, without affecting the vaccine's initial *Salmonella* colonization and its subsequent ability to protect against a *Salmonella* Heidelberg challenge in broiler chicken. The study indicates that there may even be an additive effect to having both the vaccine and the *Bacillus* composition (Table 20).

Definitions

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

Animal feed: The term "animal feed" refers to any compound, preparation, or mixture suitable for, or intended for intake by an animal. Animal feed for a monogastric animal comprises concentrates as well as for example vitamins, minerals, enzymes, amino acids and/or other feed ingredients (such as in a premix). The animal feed may further comprise forage. Examples of poultry feed are given in Examples 3 to 7.

Composition: The term "composition" refers to a composition comprising a carrier and at least one bacterial strain as described herein. The compositions described herein may be a Direct Fed Microbial (DFM), an animal feed additive or premix, or an animal feed.

Concentrate: The term "concentrate" means a feed with high protein and energy concentrations, such as fish meal, molasses, oligosaccharides, sorghum, seeds and grains (either whole or prepared by crushing, milling, etc. from, e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control *C. perfringens* infections and/or necrotic enteritis: The term "control *C. perfringens* infections and/or necrotic enteritis" means a method and/or composition that partly or completely inhibits *C. perfringens* infections and/or necrotic enteritis in an animal. Accordingly, the term "control *C. perfringens* infections and/or necrotic enteritis" means the *C. perfringens* infections and/or the necrotic enteritis are reduced or completely eliminated.

Direct Fed Microbial: The term "direct fed microbial" or "DFM" means live micro-organisms including spores which, when administered in adequate amounts, confer a benefit, such as improved digestion or health, on the host.

Enzymatic activity under anaerobic conditions: The term "enzymatic activity under anaerobic conditions" means activity of enzymes produced by a *Bacillus* strain during growth under anaerobic conditions. Example 4 of WO2013/153159 describes a method of 5 testing the *Bacillus* strains for production of the enzymes xylanase, cellulose and protease.

European Production Efficacy Factor (EPEF): The European Production Efficacy Factor is a way of comparing the live-bird performance of flocks. This single-figure facilitates comparison of performance within and among farms and can be used to assess environmental, climatic and management variables. The EPEF is calculated as [(liveability (%)× Liveweight (kg))/(Age of depletion (days)×FCR)]×100, wherein liveability is the percentage of birds alive at end of study, Liveweight is the average weight gain of the birds at end of study, age of depletion is the age of the birds at end of study and FCR is the feed conversion ratio at end of study.

Effective amount/concentration/dosage: The terms "effective amount", "effective concentration", or "effective dosage" are defined as the amount, concentration, or dosage of the bacterial strain(s) sufficient to improve the digestion or yield of an animal. The actual effective dosage in absolute numbers depends on factors including: the state of health of the animal in question, other ingredients present. The "effective amount", "effective concentration", or "effective dosage" of the bacterial strains may be determined by routine assays known to those skilled in the art. An example of an effective amount for poultry is given in Examples 3, 4, 5, 6, and 7.

Feed Conversion Rate (FCR): FCR is a measure of an animal's efficiency in converting feed mass into increases of the desired output. Animals raised for meat—such as swine, poultry, cattle, sheep and fish—the output is the mass gained by the animal. Specifically FCR is the mass of the food eaten divided by the output, all over a specified period. FCR can be determined as described in Example 7. Improvement in FCR means reduction of the FCR value.

Feeding an animal: The terms "feeding an animal" or "fed to an animal" means that the composition of the present invention is administered orally to the animal in an effective amount. The oral administration may be repeated, e.g. one or more times daily over a specified time period such as several days, one week, several weeks, one months or several months. Feeding of poultry can, e.g. be performed as described in Examples 3, 4, 5, 6, and 7. Accordingly, the terms "feeding" or "fed" mean any type of oral administration such as administration via an animal feed or via drinking water or, in certain circumstances, by oral gavage or aerosol spray.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover, straw from wheat, barley, oat, rye and other grains), residues from vegetables like beet tops, residues from oilseed production like stems and leaves from soy beans, rapeseed and other legumes, and fractions from the refining of grains for animal or human consumption or from fuel production or other industries.

Inhibitory activity against *Clostridium perfringens*: The term "Inhibitory activity against *Clostridium perfringens*" means that the growth of *Clostridium perfringens* is inhibited and/or that some or all of the *Clostridium perfringens* are killed. This can be determined by the assay described in Example 1.

Inhibitory activity against *E. coli*: The term "Inhibitory activity against *E. coli*" means that the growth of *E. coli* is inhibited and/or that some or all of the *E. coli* are killed. This can be determined by the assay described in Example 1.

Isolated: The term "isolated" means that the bacterial strains described herein are in a form or environment which does not occur in nature, i.e. the strain is at least partially removed from one or more or all of the naturally occurring constituents with which it is associated in nature.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Poultry: The term "poultry" means domesticated birds kept by humans for the eggs they produce and/or their meat and/or their feathers. Poultry includes breeders, broilers and layers. Poultry include members of the superorder Galloanserae (fowl), especially the order Galliformes (which includes chicken, Guineafowls, quails and turkeys) and the family Anatidae, in order Anseriformes, commonly known as "waterfowl" and including domestic ducks and domestic geese. Poultry also includes other birds that are killed for their meat, such as pigeons and ostriches. Examples of poultry include chicken (including layers, broilers and chicks), ducks, geese, pigeons, turkeys and quail.

Prevent *C. perfringens* infections and/or necrotic enteritis: The term "prevent *C. perfringens* infections and/or necrotic enteritis" means a method and/or composition that prevents development of a *C. perfringens* infection and/or necrotic enteritis in an animal.

Reducing sugar: A reducing sugar is any sugar that either has a reactive aldehyde group or is capable of forming one to allow the sugar to act as a reducing agent. The reducing ends are formed by the enzymatic cleavage of the glycosidic bond between polymeric carbohydrates. Reducing sugars include glucose, glyceraldehyde and galactose as well as disaccharides, like lactose and maltose and can be measured by the Nelson-Somogyi (NS) or dintrosalicylic acid (DNS) method. DNS is an aromatic compound that reacts with reducing sugars and other reducing molecules to form 3-amino-5-nitrosalicylic acid, which absorbs light strongly at 540 nm. The assay simulates the situation when feed is ingested by the animal and is digested in the digestive tract. The ability of different *Bacillus* strains to degrade Non Starch Polysaccharides (NSP) to reducing sugars has been investigated in Example 2.

Roughage: The term "roughage" means dry plant material with high levels of fiber, such as fiber, bran, husks from seeds and grains and crop residues (such as stover, copra, straw, chaff, sugar beet waste).

Sensitive to antibiotics: The term "sensitive to antibiotics" means the phenotypic property of a bacterial strain, that growth of said bacterial strain is inhibited under conditions where the bacterial strain would otherwise grow. In this context sensitivity to antibiotics is tested after the CLSI guidelines (M07-A8 and M45-A2). A strain of *Bacillus* is considered sensitive if growth is only detected at or below the breakpoint concentration specified in EFSA Journal 2012; 10(6):2740 for vancomycin, gentamicin, kanamycin, streptomycin, erythromycin, clindamycin, tetracycline, and chloramphenicol. With regard to ampicillin there is no breakpoint given by EFSA for *Bacillus*; the breakpoint 4 mg/L has been chosen for a strain to be considered sensitive.

Silage: The term "silage" means fermented, high-moisture stored fodder which can be fed to herbivores such as horses and ruminants e.g. camels, lama, cattle and sheep, or used as a biofuel feedstock for anaerobic digesters. It is fermented and stored in a process called ensilage, ensiling or silaging, and is usually made from grass or cereal crops (e.g. maize, sorghum, oats, rye, timothy, forage grass plants) or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Spore: The terms "spore" and "endospore" are interchangeable and have their normal meaning which is well known and understood by those of skill in the art. As used herein, the term spore refers to a microorganism in its dormant, protected non-reproductive state.

Stable: The term "stable" is a term that is known in the art, and in a preferred aspect, stable is intended to mean the ability of the microorganism to remain in a live form until it is administered to an animal to improve the health of the animal.

Swine: The term "swine" or "pigs" means domesticated pigs kept by humans for food, 20 such as their meat. Swine includes members of the genus Sus, such as Sus scrofa domesticus or Sus domesticus and includes piglets, weaners, growers, finishers, hocks, polts, gilts, sows, and gestation sows.

Vegetable protein: The term "vegetable protein" refers to any compound, preparation or mixture that includes at least one protein derived from or originating from a vegetable, including modified proteins and protein-derivatives.

Vegetable proteins may be derived from vegetable protein sources, such as legumes and cereals, for example materials from plants of the families Fabaceae (Leguminosae), e.g. soybean, lupine, pea, or bean; Cruciferaceae, Chenopodiaceae, e.g. beet, sugar beet, spinach or quinoa; and Poaceae. Other examples of vegetable protein sources are cereals such as barley, wheat, rye, oat, maize (corn), rice, and sorghum.

Weight Gain: The Weight Gain of an animal is the increase of weight of the animal over a specified time period. An example of average Weight Gain determination is given in Example 3 and an example of daily Weight Gain determination is given in Example 7.

DETAILED DISCLOSURE OF THE INVENTION

The present invention provides a *Bacillus subtilis* strain selected from the group consisting of the strain deposited as DSM32324, the strain deposited as DSM32325, and 5 a mutant strain of DSM32324 or DSM32325 which has sensitivity for ampicillin, vancomycin, gentamicin, kanamycin, streptomycin, erythromycin, clindamycin, tetracycline, and chloramphenicol; and has inhibitory activity against *E. coli* and *Clostridium perfringens*.

The bacterial strains described herein are isolated, i.e. present in a form or environment which does not occur in nature.

A "mutant bacterium" or a "mutant strain" refers to a natural (spontaneous, naturally occurring) mutant bacterium or an induced mutant bacterium comprising one or more mutations in its genome (DNA) which are absent in the parent strain DNA. An "induced mutant" is a bacterium where the mutation was induced by human treatment, such as treatment with any conventionally used mutagenization treatment including treatment with chemical mutagens, such as a chemical mutagen selected from (i) a mutagen that associates with or become incorporated into DNA such as a base analogue, e.g. 2-20 aminopurine or an interchelating agent such as ICR-191, (ii) a mutagen that reacts with the DNA including alkylating agents such as nitrosoguanidine or hydroxylamine, or ethane methyl sulphonate (EMS) or N-methyl-N'-nitro-N-nitroguanidine (NTG), UV- or gamma radiation etc. In contrast, a "spontaneous mutant" or "naturally occurring mutant" has not been mutagenized by man.

A mutant may have been subjected to several mutagenization treatments (a single treatment should be understood one mutagenization step followed by a screening/selection step), but it is presently preferred that no more than 20, or no more than 10, or no more than 5 treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

Mutant bacteria as described above are non-GMO, i.e. not modified by recombinant DNA technology. As an alternative to the above preferred method of providing the mutant by random mutagenesis, it is also possible to provide such a mutant by site-directed mutagenesis, e.g. by using appropriately designed cloning techniques.

When the mutant is provided as a spontaneously occurring mutant, the strain is subjected to the selection step without any preceding mutagenization treatment.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the nucleotide sequence of DSM32324.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the amino acid sequence of DSM32324.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the nucleotide sequence of DSM32325.

In one embodiment, the *Bacillus subtilis* strain of the invention has at least 98% (such as at least 98.5%, such as at least 99%, such as at least 99.5%, such as at least 99.6%, such as at least 99.7%, such as at least 99.8%, such as at least 99.9%) sequence identity to the amino acid sequence of DSM32325.

A *Bacillus* strain is considered to exhibit an inhibitory activity towards *E. coli* if the inhibition zone is at least 0.5 mm (low inhibition). Preferably, the inhibition zone is at between at least 0.5 mm and 2 mm (medium), more preferably more than 2 mm (high). The inhibition zone may be different for the various *E. coli* strains. For a strain to be considered to exhibit an inhibitory activity against *E. coli* according to the present invention it should exhibit an inhibition zone of at least 0.5 mm for all of the *E. coli* strains tested. Preferably, the inhibition zone of two, three, four or even more preferably the inhibition zone of all five of the *E. coli* strains is at least between 0.5 mm and 2 mm. Even more preferably, the inhibition zone of two, three, four or even more preferably the inhibition zone of all five of the *E. coli* strains is more than 2 mm.

A *Bacillus* strain is considered to exhibit an inhibitory activity towards *Clostridium perfringens* if the inhibition zone is at least 0.5 mm (low inhibition). Preferably, the inhibition zone is at between at least 0.5 mm and 2 mm (medium), more preferably more than 2 mm (high). The inhibition zone may be different for the various *Clostridium perfringens* strains. For a strain to be considered to exhibit an inhibitory activity against *Clostridium perfringens* according to the present invention it should exhibit an inhibition zone of at least 0.5 mm for all of the *Clostridium perfringens* strains tested. Preferably, the inhibition zone of two, three, four or even more preferably the inhibition zone of all five of the *Clostridium perfringens* strains is at least between 0.5 mm and 2 mm. Even more preferably, the inhibition zone of two, three, four or even more preferably the inhibition zone of all five of the *Clostridium perfringens* strains is more than 2 mm.

Preferably, a *Bacillus* strain should also be able to increase the amount of reducing sugars from degradation of Non Starch Polysaccharides (NSP). The ability of different *Bacillus* strains to degrade NSP to reducing sugars has been investigated in Example 2 and the results are provided in Table 4. Strains having the ability to increase the available sugar amount to at least 500 kJ/kg feed when tested as outlined in the example are considered preferable.

Based on the detailed assay descriptions the person of ordinary skill in the art is able to repeat these assays to determine whether a specific *Bacillus* strain complies with the antibiotic sensitivity, the inhibitory activity and the capability of degrading NSP. In this manner the person of ordinary skill in the art will be able to consistently produce strains with the stated properties. Preferably, the person of skill in the art will also include assaying for sensitivity of the vegetative cells at pH 4, and assaying for bile resistance to ensure that the strains are able to survive to a sufficient degree in the gastrointestinal tract e.g. as described in WO2013/153159. Evidently, these assays can be performed in any order and some strains may be excluded during the process if they do not fulfill the criteria.

The invention further provides a *Bacillus* composition comprising at least one *Bacillus subtilis* strain of the invention. In one embodiment, the *Bacillus* composition comprises one *Bacillus subtilis* strain of the invention. In another embodiment, the *Bacillus* composition comprises two *Bacillus subtilis* strains of the invention, for example a combination of *Bacillus subtilis* DSM32324 and *Bacillus subtilis* DSM32325.

The *Bacillus* compositions according to the invention may comprise a combination of at least one of the *Bacillus subtilis* strains of the invention and at least one other *Bacillus* strain. The *Bacillus* composition may comprise at least two strains, such as at least three, such as at least four, such as at least five *Bacillus* strains, at least one of which is a *Bacillus subtilis* strain of the present invention.

*Bacillus* strains may be used in any combination in the *Bacillus* compositions. For example, the *Bacillus* composition may comprise at least one *Bacillus subtilis* strain of the invention and/or at least one *Bacillus licheniformis* strain and/or at least one *Bacillus amyloliquiefaciens* strain e.g. two *Bacillus subtilis* strains of the invention and at least one *Bacillus amyloliquiefaciens* strain. The composition may comprise *Bacillus subtilis* DSM32324 and/or *Bacillus subtilis* DSM32325 in combination with *Bacillus amyloliquiefaciens* DSM25840 and/or *Bacillus licheniformis* DSM17236 and/or *Bacillus subtilis* DSM19489. Any other possible combination of the *Bacillus* strains of the present invention with other *Bacillus* strains may also be made. As a specific example, the *Bacillus* composition comprises *Bacillus subtilis* DSM32324, *Bacillus subtilis* DSM32325 and *Bacillus amyloliquiefaciens* DSM25840. As another specific example, the *Bacillus* composition comprises *Bacillus subtilis* DSM32324, *Bacillus subtilis* DSM32325 and *Bacillus licheniformis* DSM17236. In a yet further specific example, the *Bacillus* composition comprises *Bacillus subtilis* DSM32324, *Bacillus subtilis* DSM32325 and *Bacillus subtilis* DSM19489.

If more than one strain is used, it is contemplated that the proportion of each strain in the composition will be 1 to 99%, such as 20 to 80%, e.g. 30 to 70%, more particularly 20%, 33%, 40% or 50% of the total amount of bacterial isolates calculated as CFU/g composition. The individual strains may be present in about equal numbers or in unequal numbers.

A presently preferred embodiment of the invention is a *Bacillus* composition comprising DSM32324, DSM25840 and DSM32325 in a ratio of 8:3:5.

The relevant *Bacillus* strain or strains are provided in a commercially relevant form known to the skilled person. Accordingly, in an embodiment the *Bacillus* strain or strains of the composition are present in a dried (e.g. spray dried) or frozen form. The composition may be provided in any suitable form such as in the form of a liquid e.g. a gel, a slurry, a powder or a pellet.

In a preferred embodiment, the *Bacillus* composition comprises from $10^5$ to $10^{12}$ CFU/g, such as from $5 \times 10^5$ to $10^{12}$ CFU/g, more preferably from $10^6$ to $10^{12}$ CFU/g, and most preferably from $10^2$ to $10^{12}$ CFU/g, such as from $10^8$ to $10^{11}$ CFU/g, e.g. from $10^9$ to $10^{10}$ CFU/g of each of the bacterial strains in the composition. The *Bacillus* composition comprises at least $5 \times 10^4$ CFU of each strain per gram of the composition which distinguishes a composition of the present invention from e.g. animal feed with naturally occurring strains.

The term "CFU/g" relates to the gram weight of the composition including carriers such as calcium carbonate, anti caking agents such as aluminum silicates and kieselgur (diatomaceous earth), and other components present in the composition.

Compositions of the present invention include at least one *Bacillus* strain of the invention and at least one carrier and/or other component that make the composition suitable for feeding to an animal or as an additive for drinking water.

As used herein the term "premix" refers to a *Bacillus* strain added to a carrier to make a premix which is then added to an animal feed at a desired inclusion rate.

Alternatively, at least one *Bacillus* strain of the invention may be formulated with animal feed ingredients as discussed in detail in the following. Such combinations may be in the form of pellets that are extruded through standard pelleting processes.

The invention also provides a method for producing an animal feed, animal feed additive or premix comprising adding at least one *Bacillus* strain of the invention to an animal feed or relevant components thereof.

*Bacillus* bacteria exist as spores and vegetative cells which can divide to produce more vegetative cells. When reference is made herein to *Bacillus*, this relates to both spores and vegetative cells unless the context indicates otherwise.

In the *Bacillus* composition of the present invention, the *Bacillus* strain or strains are preferably provided as spores. The primary function of sporulation is generally to ensure the survival of a bacterium through periods of environmental stress. They are therefore resistant to ultraviolet and gamma radiation, desiccation, lysozyme, temperature, starvation, and chemical disinfectants. The spore coat is impermeable to many toxic molecules and may also contain enzymes that are involved in germination. The core has normal cell structures, such as DNA and ribosomes, but the spore is metabolically inactive.

The vegetative form of the bacteria produces effectors which may reduce bacterial pathogens or have other beneficial effects in the gastrointestinal tract of an animal. Thus, reactivation and germination of the spores after administration to the animal is important.

It is known from the literature that bile has some negative influences on the survival and germination and outgrowth to vegetative cells in the GIT of animals. Therefore probiotic bacteria shall generally be able to survive and proliferate in the gut of animals by being able to tolerate a low pH and resistant to bile salt in order to be useful as probiotic *Bacillus* compositions for the addition to animal feed. The examples provide useful in vitro tests in this regard. The test for sensitivity to low pH (simulating gastric conditions) focuses on the resistance of vegetative cells to pH 4. It is well known that spores are resistant at pH values of 2-3 and that vegetative cells will die at pH 2. However, gastric pH may have pH values of up to 4 especially in feeding conditions. This may result in germination of the spores and it is thus relevant to test the sensitivity of vegetative cells at pH 4. Selected strains should preferably be resistant to pH at 4.

The *Bacillus subtilis* strains deposited as DSM32324 and DSM32325 have been assayed for sensitivity of the vegetative cells at pH 4 and bile resistance to ensure that the strains are suitable.

A *Bacillus* composition may comprise one or two different strains of *B. subtilis* and/or one or two strains of *B. licheniformis* and/or one or two strains of *Bacillus amyloliquefaciens*, wherein each strain is independently selected to perform a specific role and/or function. The combination of these strains can be combined with an animal feed, such as poultry feed, and ultimately used to improve the health and productivity of the agricultural animals (e.g. livestock and/or poultry). For example the strains and/or the combined strains can reduce gut pathogens in the poultry and increase weight gain of commercial poultry.

In a further embodiment, the *Bacillus* composition of the invention can be combined with a vaccine, such as a live *Salmonella* Typhimurium vaccine, to reduce infection by *Salmonella* and/or increase FCR.

In one aspect, the present invention provides an an animal feed, animal feed additive or premix comprising at least one *Bacillus subtilis* strain according to the invention, and further comprising one or more of concentrate(s), vitamin(s), mineral(s), enzyme(s), amino acid(s) and/or other feed ingredient(s). In one embodiment the animal feed, animal feed additive or premix comprises the *Bacillus subtilis* strain DSM32324. In another embodiment the animal feed, animal feed additive or premix comprises the *Bacillus subtilis* strain DSM32325. The animal feed, animal feed additive or premix may comprise both *Bacillus subtilis* DSM32324 and *Bacillus subtilis* DSM32325.

In a specific embodiment, the animal feed comprises forage. Generally, the forage comprises a vegetable protein source. In a particular embodiment, the vegetable protein source is material from one or more plants of the family Fabaceae. In another particular embodiment, the vegetable protein source is material from one or more plants of the family Chenopodiaceae. Other examples of vegetable protein sources are rapeseed and cabbage. In another particular embodiment, soybean is a preferred vegetable protein source. As an example, the forage comprises 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

In one embodiment, the forage and at least one *Bacillus subtilis* strain of the invention are mixed with a concentrate. In another embodiment, the forage and at least one *Bacillus subtilis* strain of the invention are mixed with a premix. In a further embodiment, the forage and at least one *Bacillus subtilis* strain of the invention are mixed with vitamins and/or minerals. In a further embodiment, the forage and at least one *Bacillus subtilis* strain of the invention are mixed with one or more enzymes. In a further embodiment, the forage and at least one *Bacillus subtilis* strain of the invention are mixed with other feed ingredients, such as colouring agents, stabilisers, growth improving additives and aroma compounds/flavorings, polyunsaturated fatty acids (PU-FAs); reactive oxygen generating species, anti-microbial peptides, anti-fungal polypeptides and amino acids.

In a particular embodiment, the animal feed consists of or comprises milk (e.g. from sow, cow, goat, sheep), e.g. for feeding of piglets. In another particular embodiment, the animal feed consists of or comprises milk replacement, e.g. for feeding of piglet.

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals. Usually fat- and water-soluble vitamins, as well as trace minerals form part of a so-called premix intended for addition to the feed, whereas macro minerals are usually separately added to the feed. Non-limiting examples of fat-soluble vitamins include vitamin A, vitamin D3, vitamin E, and vitamin K, e.g. vitamin K3. Non-limiting examples of water-soluble vitamins include vitamin B12, biotin and choline, vitamin B1, vitamin B2, vitamin B6, niacin, folic acid and panthothenate, e.g. Ca-D-panthothenate. Non-limiting examples of trace minerals include boron, cobalt, chloride, chromium, copper, fluoride, iodine, iron, manganese, molybdenum, selenium and zinc. Non-limiting examples of macro minerals include calcium, magnesium, potassium and sodium.

The animal feed, animal feed additive or premix of the invention may also comprise at least one enzyme selected from the group comprising of phytase (EC 3.1.3.8 or 3.1.3.26); xylanase (EC 3.2.1.8); galactanase (EC 3.2.1.89); alpha-galactosidase (EC 5 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

The animal feed, animal feed additive or premix of the invention may further comprise one or more added amino acids. Examples of amino acids which are used in animal feed are lysine, alanine, beta-alanine, threonine, methionine and tryptophan. The animal feed, animal feed additive or premix of the invention may further comprise colouring agents, stabilisers, growth improving additives and aroma compounds/flavorings, polyunsaturated fatty acids (PUFAs); reactive oxygen generating species, anti-microbial peptides and anti-fungal polypeptides. Examples of colouring agents are carotenoids such as beta-carotene, astaxanthin, and lutein. Examples of aroma compounds/flavorings are creosol, anethol, deca-, undeca-and/or dodeca-lactones, ionones, irone, gingerol, piperidine, propylidene phatalide, butylidene phatalide, capsaicin and tannin. Examples of polyunsaturated fatty acids are C18, C20 and C22 polyunsaturated fatty acids, such as arachidonic acid, docosohexaenoic acid, eicosapentaenoic acid and gamma-linoleic acid. Examples of reactive oxygen generating species are chemicals such as perborate, persulphate, or percarbonate; and enzymes such as an oxidase, an oxygenase or a syntethase.

In one embodiment the animal feed, animal feed additive or premix comprises one or more coccidiostats.

The animal feed, animal feed additive or premix further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, whey, whey permeate, wheat flour, wheat bran, corn gluten meal, starch and cellulose.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 70° C. to 120° C.

In an embodiment, the animal feed, animal feed additive or premix further comprises one or more additional microorganisms. In a particular embodiment, the animal feed, animal feed additive or premix further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a particular embodiment, the animal feed, animal feed additive or premix further comprises a bacterium from one or more of the following strains of *Bacillus amyloliquefaciens, Bacillus subtilis, Bacillus pumilus, Bacillus polymyxa, Bacillus licheniformis, Bacillus megaterium, Bacillus coagulans, Bacillus circulans, Bacillus simplex, Bacillus mojavensis, Bacillus safensis, Bacillus simplex, Bacillus atrophaeus, Bacillus methylotrophicus, Bacillus siamensis, Bacillus vallismortis, Bacillus tequilensis*. or any combination thereof.

In a particular embodiment, the animal feed, animal feed additive or premix further comprises one or more types of yeast. The one or more types of yeast can be selected from the group consisting of *Saccharomycetaceae, Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and *Basidiomycota*.

Animal diets can, e.g. be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) *Bacillus* composition may also be added before or during the feed ingredient step. Typically a liquid *Bacillus* composition of the invention comprises the bacterial strain(s) optionally with a polyol, such as glycerol, ethylene glycol or propylene glycol, and is added after the pelleting step, such as by spraying the liquid formulation onto the pellets. The bacteria may also be incorporated in an animal feed additive or premix.

The composition according to the invention may be used for the prevention or control of a bacterial colonization or infection, e.g. by *E. coli* and/or *Clostridium*, such as *Clostridium difficile, Clostridium novyi, Clostridium perfringens*, or *Clostridium septicum*.

In another aspect, the invention relates to a method for the prevention or control of a bacterial colonization or infection, e.g. by *E. coli* and/or *Clostridium*, such as *Clostridium difficile, Clostridium novyi, Clostridium perfringens, or Clostridium septicum*, the method comprising administering an effective amount of a strain according to the invention or a composition according to the invention to an animal in need thereof.

Another aspect of the invention relates to a method for feeding an animal comprising administering a *Bacillus* composition of the invention to an animal, in particular a monogastric animal.

Monogastric animals include, but are not limited to, poultry such as broilers, breeders, layers, turkey, ostriches, quails, ducks, and geese, herbivores, such as horses and ruminants, e.g. camels, lamas, cattle and sheep, calves, swine, such as piglets, weaners, growers, finishers, hocks, polts, gilts, sows, gestation sows, rodents such as rabbits, pets such as cats and dogs and fish (including but not limited to salmon, trout, tilapia, catfish and carps; and crustaceans (including but not limited to shrimps and prawns). Pigs and/or poultry are preferred monogastric animals.

In another aspect, the invention relates to the use of at least one *Bacillus subtilis* strain of the invention or an animal feed, animal feed additive or premix comprising at least one *Bacillus subtilis* strain of the invention to improve the performance of an animal, in particular a monogastric animal As evidenced in the examples, administration of a *Bacillus subtilis* strain of the invention improves the gastrointestinal health of the animal, e.g. prevent or control enteritis, and provides improved animal performance parameters for the treated animals as compared to controls. Animal performance parameters include but are not limited to weight gain (WG), feed conversion rates (FCR), decrease of mortality and increase of European Production Efficacy Factor (EPEF).

The invention further provides a method of increasing digestibility of an animal feed, such as protein digestibility, the method comprising feeding a strain according to the invention or a composition according to the invention to an animal.

Accordingly, the invention relates to use of a strain according to the invention, or a composition according to the invention, for improving one or more animal performance parameters selected from the group consisting of:
 i) increased weight gain (WG),
 ii) lower feed conversion ratio (FCR),
 iii) lower necrotic enteritis lesion scoring,
 iv) lower necrotic enteritis frequency,
 v) lower necrotic enteritis mortality,
 vi) increased European Production Efficacy Factor (EPEF), and
 vii) lower mortality.

In a preferred embodiment of the invention, "animal performance" is determined by the body weight gain of the animal and/or by the feed conversion ratio. By "improved animal performance" it is meant that there is increased body weight gain and/or reduced feed conversion ratio and/or improved digestibility of nutrients or digestible energy in a feed and/or metabolizable energy and/or increased feed efficiency resulting from the use of animal feed, animal feed additive or premix of the present invention in animal feed in comparison to animal feed which does not comprise said animal feed, animal feed additive or premix. Preferably, by "improved animal performance" it is meant that there is increased body weight gain and/or reduced feed conversion ratio.

An "increased weight gain" refers to an animal having increased body weight on being fed feed comprising a feed composition compared with an animal being fed a feed without said feed composition of the invention. Specifically, the Weight Gain (WG) of an 30 animal is the increase of weight of the animal over a specified time period. In one embodiment, the improvement in body weight gain is of at least 0.5%, such as at least 1%, such as at least 2%, such as at least 2.5%, such as at least 3%, such as at least 4%, such as at least 5%, such as at least 6%, such as at least 7%, such as at least 8%, such as at least 9%, such as at least 10%.

In one embodiment, the improvement in weight gain results in a body weight gain of at least 0.5%, such as at least 0.8%, such as at least 1.2%, such as at least 1.5%, such as at least 1.8%, such as at least 2.0%, such as at least 2.5%, such as at least 3.0%, such as at least 4.0%, such as at least 5.0%, such as at least 6.0%, such as at least 7.0%. In a preferred embodiment, the improvement in weight gain results in a weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

In one embodiment, the improvement of feed conversion ratio (FCR) results in a FCR of −2.5% or less than −2.5%, such as less than −2.6%, such as less than −2.7%, such as less than −2.8%, such as less than −2.9%, such as less than −3.0%. In a preferred embodiment, the improvement of FCR results in a FCR of from −5% to −2%, such as a FCR of from −4% to −2%, such as a FCR of from −3.5% to −2.5%. In a specific embodiment, the improvement of FCR results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals.

Nutrient digestibility as used herein means the fraction of a nutrient that disappears from the gastrointestinal tract or a specified segment of the gastrointestinal tract, e.g. the small intestine. Nutrient digestibility may be measured as the difference between what is administered to the subject and what comes out in the faeces of the subject, or between what is administered to the subject and what remains in the digesta on a specified segment of the gastrointestinal tract, e.g. the ileum. Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastrointestinal tract or a segment of the gastrointestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, mineral digestibility and amino acid digestibility.

In another embodiment, the invention relates to a method of improving one or more animal performance parameters selected from the group consisting of
 i) increased weight gain (WG),
 ii) lower feed conversion ratio (FCR),
 iii) lower necrotic enteritis lesion scoring,
 iv) lower necrotic enteritis frequency,
 v) lower necrotic enteritis mortality,
 vi) increased European Production Efficacy Factor (EPEF), and
 vii) lower mortality, the method comprising feeding a strain according to the invention or a composition according to the invention to an animal.

A composition of the present invention may also be used for flexible feed formulation (FFF) wherein an animal is being fed with a feed having a reduced metabolizable energy and a composition of the invention whereby an acceptable animal performance and or feed conversion ratio is obtained in spite of the reduced metabolizable energy in the feed. The reduced metabolizable energy may be in the level of from 97% to 99% of standard feed for the animal in question, such as from 97% to 98% or from 98% to 99%.

Deposit and Expert Solution

The *Bacillus licheniformis* strain DSM17236 has been deposited at DSMZ (Deutsche Sammlung von Mikroorganismen und Zellkulturen GmbH, Inhoffenstrasse 7B, D-38124 Braunschweig) on Apr. 7, 2005 by Chr. Hansen A/S, Denmark. The deposit has been made under the conditions of the Budapest Treaty on the International Recognition of the Deposit of Microorganisms for the Purposes of Patent Procedure.

The *Bacillus subtilis* strain DSM19489 has been deposited at DSMZ (Deutsche Sammlung von Mikroorganismen und Zellkulturen GmbH, Inhoffenstrasse 7B, D-38124 Braunschweig) on Jun. 27, 2007 by Chr. Hansen A/S, Denmark. The deposit has been made under the conditions of the Budapest Treaty on the International Recognition of the Deposit of Microorganisms for the Purposes of Patent Procedure.

The *Bacillus mojavensis* strain DSM25839 has been deposited at DSMZ (Deutsche Sammlung von Mikroorganismen und Zellkulturen GmbH, Inhoffenstrasse 7B, D-38124 Braunschweig) on Apr. 3, 2012 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain DSM25840 was deposited and accepted at Leibniz-Insitut DSMZ (Deutsche Sammlung von Mikroorganismen und Zellkulturen GmbH, Inhoffenstrasse 7B, D-38124 Braunschweig, Germany) on Apr. 3, 2012, under the terms of the Budapest Treaty on the International Recognition of the Deposit of Microorganisms for the Purposes of Patent Procedure and in compliance with 37 C.F.R. 1.801-1.809. It is to be understood that the availability of a deposit does not constitute a license to practice the presently claimed subject matter in derogation of patent rights granted by governmental action.

The *Bacillus subtilis* strain DSM25841 has been deposited DSMZ (Deutsche Sammlung von Mikroorganismen und Zellkulturen GmbH, Inhoffenstrasse 7B, D-38124 Braunschweig) on Apr. 3, 2012 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain DSM27032 has been deposited at DSMZ (Deutsche Sammlung von Mikroorganismen und Zellkulturen GmbH, Inhoffenstrasse 7B, D-38124 Braunschweig) on Mar. 21, 2013 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain DSM32324 was deposited and accepted at Leibniz-Insitut DSMZ (Deutsche Sannnnlung von Mikroorganismen und Zellkulturen GmbH, Inhoffenstrasse 7B, D-38124 Braunschweig, Germany) on Jun. 8, 2016, under the terms of the Budapest Treaty on the International Recognition of the Deposit of Microorganisms for the Purposes of Patent Procedure and in compliance with 37 C.F.R. 1.801-1.809. It is to be understood that the availability of a deposit does not constitute a license to practice the presently claimed subject matter in derogation of patent rights granted by governmental action.

The *Bacillus amyloliquefaciens* strain DSM32325 was deposited and accepted at Leibniz-Insitut DSMZ (Deutsche Sannnnlung von Mikroorganismen und Zellkulturen GmbH, Inhoffenstrasse 7B, D-38124 Braunschweig, Germany) on Jun. 8, 2016, under the terms of the Budapest Treaty on the International Recognition of the Deposit of Microorganisms for the Purposes of Patent Procedure and in compliance with 37 C.F.R. 1.801-1.809. It is to be understood that the availability of a deposit does not constitute a license to practice the presently claimed subject matter in derogation of patent rights granted by governmental action.

For all of the above-identified deposited microorganisms, the following additional indications apply:

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

IN VITRO EXAMPLES

Example 1

Screening for Pathogen Inhibition and Antibiotic Sensitivity

Materials

Veal Infusion Broth (VIB) (Difco, 234420)
Veal Infusion Broth (VIB) agar (VIB +1.5% Agar bacteriological (Agar no. 1), Oxoid LP0011)
Muller Hinton Broth 2, Cation-adjusted (Fluka)
T3 agar plates (per liter: 3 g of tryptone, 2 g of tryptose, 1.5 g of yeast extract, 0.05 M sodium dihydrogen phosphate and 0.005 g of MnCl2 [pH 6.8], and 15 g agar)
Laura-Bertani (LB) broth (g/L: Bacto tryptone 10 (Difco 0123), Yeast extract 5 (Oxoid 35 L21), NaCl 10 (Merck nr. 106404))
Brain Heart Infusion (BHI) agar (Oxoid CM375)
Bile salts (Bile extract, porcine; Sigma B8631)
Bioassay dishes (Nunc 240845)
Petri dishes (Procudan 140096, petridish with ribs)
Physiological saline solution with peptone (0.9% sodium chloride, 1% peptone) FKP ISO-SENSITEST Broth (Oxoid CM0473)
Microtitre plates (MTP) NUNC, Denmark
Omni tray/single well plates N 242811 Thermo Scientific/ NUNC Denmark
Deep well microtitre 96 well trays (DW) Rnase/DNase free (Thermo Fisher Science)
Ampicillin (Sigma, A9518-5G)
Vancomycin (Sigma, V1764-250MG)
Gentamicin (Sigma, G1264-50MG)

Kanamycin (Sigma, K1377-1G)
Streptomycin (Sigma, 56501-5G)
Erythromycin (Sigma E-5389)
Clindamycin (Sigma, C2569-10MG)
Tetracycline (Sigma T-7660)
Chloramphenicol (Sigma, C0378-5G)
*Escherichia coli* 0101 H-, K99 F5 (State Serum Institute, Copenhagen, Denmark)
*Escherichia coli* 0147:K89 F4 H19 (State Serum Institute, Copenhagen, Denmark) 20 *Escherichia coli* 0149:k91, k88a,c,h10 NCTC10650, (National Collection of Type Cultures, England)
*E. coli* ATCC11775 (American type culture collection)
*E. coli* Cp6salp3 (Copenhagen Veterinary University)
*Clostridium perfringens* Type A, DSM756, Leibniz-Institut DSMZ—Deutsche Sammlung von Mikroorganismen and Zellkulturen
*Clostridium perfringens* type C, NCTC3180, National Collection of Type Cultures (England)
*Clostridium perfringens* CCUG2036 (Culture Collection, University of Gothenburg, Sweden)
*Clostridium perfringens* CCUG2037 (Culture Collection, University of Gothenburg, Sweden)
*Clostridium perfringens* CCUG44727 (Culture Collection, University of Gothenburg, Sweden)

All pathogen strains mentioned above were maintained in LB with 20% glycerol in BHI at −80° C.

*Bacillus* Cultures

*Bacillus* strains isolated from feces, soil, food sources and collected from strain bank collections were maintained in VIB with 20% glycerol in MTP master plates at −80° C.

Bacteria spore-forming aerobic isolates were subjected to identification by 16S ribosomal sequence and gyrB (Wang et al., 2007), screening for antibiotic susceptibility according to "Guidance on the assessment of bacterial susceptibility to inhibitorys of human and veterinary importance." EFSA Journal 2012;10(6):2740 as described below, and bile resistance and sensitivity to low pH, enzymatic activity, growth in different media, heat resistance and sporulation as described in WO2013/153159.

Antibiotic Susceptibility Measured by MIC

*Bacillus* strains were analyzed for antibiotic susceptibility by measuring the minimum 10 inhibitory concentration (MIC) for a number of antibiotics. The method used was a broth microdilution method as outlined by the standard of CLSI (Clinical and Laboratory Standards Institute M07-A8 and M45-A2).

A suspension of an overnight culture of the strain to be tested was inoculated in ISO-SENSITEST Broth (Oxoid CM0473) in microtitre plates at an approximate concentration of $10^5$ CFU/ml (colony-forming units/ml) in two-fold serial dilutions of the antibiotic to be tested (total volume 100 μl/well) and incubated aerobically for 20-24 hours at 37° C. The results were recorded after 20 hours of incubation as the lowest concentration of the antibiotic to inhibit visible growth. The test was performed twice as two independent biological replicates.

Only *Bacillus* strains which were susceptible to inhibitorys according to the EFSA Guidance were included in the screening for inhibition of pathogenic *E. coli* and *Clostridium perfringens*.

Screening *of Bacillus* Strains for Inhibition of Pathogenic *E. coli*

*Bacillus* strains were added in a volume of 50 pl from MTP master plates into 700 μl VIB in DW plates and incubated at 37° C. and 175 rpm overnight. *E. coli* strains were grown in LB at 30° C. overnight. 2 ml of *E. coli* overnight culture was mixed with 200 ml liquid VIB agar at 50° C., and poured into each bioassay dish. The dishes were dried in a sterile bench. Overnight *Bacillus* cultures, 2 pl of each, were spotted onto the surface of the VIB agar mixed with *E. coli* in the bioassay dishes and incubated at 37° C. for 1 day.

Radii of clarified inhibition zones around the *Bacillus* were measured and recorded as "3 =high"—more than 2 mm, "2=medium"—between 0.5-2 mm and "1=low"—less than 0.5 mm and 0=no inhibition.

Clostridium Perfringens Inhibition by Agar Spot Test

VIB agar was poured into bioassay dishes (200 ml per dish) and dried thoroughly in a sterile bench. Overnight *Bacillus* cultures, 2 μl of each, were spotted onto the surface of the VIB agar dishes and incubated at 37° C. overnight. *Clostridium perfringens* strains were grown anaerobically on BHI agar at 37° C. overnight. Overnight culture of *Clostridium perfringens* was added in a volume of 2 ml to 200 ml liquid BHI agar, mixed and overlaid gently into the bioassay dishes with *Bacillus* spots. The dishes were incubated anaerobically at 37° C. for 1 day.

Radii of clarified inhibition zones around the *Bacillus* were measured and recorded as "3 =high"—more than 2 mm, "2=medium"—between 0.5-2 mm and "1=low"—less than 0.5 mm and 0=no inhibition.

All data were replicated on separate days.

Results

TABLE 1

Results of selected *Bacillus* strains' inhibition of *E. coli*

| Inhibition | DSM number if available | *E. coli* inhibition | | | | |
|---|---|---|---|---|---|---|
| | | *E. coli* O101 F5 | *E. coli* O147:K89 F4 | *E. coli* O149:k91, k88a | *E. coli* ATCC 11775 | *E. coli* Cp6salp3 |
| *Bacillus licheniformis* | | 0 | 0 | 0 | 0 | 0 |
| *Bacillus licheniformis* | 17236 | 0 | 0 | 0 | 0 | 0 |
| *Bacillus subtilis* | 19489 | 0 | 0 | 0 | 0 | 0 |
| *Bacillus subtilis* | | 0 | 0 | 1 | 1 | 1 |
| *Bacillus subtilis* | 32324 | 3 | 3 | 3 | 3 | 3 |

TABLE 1-continued Results of selected Bacillus strains' inhibition of E. coli

| Inhibition | DSM number if available | E. coli O101 F5 | E. coli O147:K89 F4 | E. coli O149:k91, k88a | E. coli ATCC 11775 | E. coli Cp6salp3 |
|---|---|---|---|---|---|---|
| Bacillus subtilis | | 0 | 0 | 0 | 0 | 0 |
| Bacillus subtilis | | 0 | 0 | 0 | 0 | 0 |
| Bacillus subtilis | 32325 | 2 | 2 | 3 | 2 | 2 |
| Bacillus subtilis | 25841 | 2 | 2 | 2 | 2 | 2 |
| Bacillus amyloliquefaciens | 25840 | 1 | 1 | 2 | 1 | 1 |
| Bacillus amyloliquefaciens | 27032 | 2 | 3 | 3 | 2 | 2 |

TABLE 2

Results of selected Bacillus strains' inhibition of Clostridium

| Inhibition | DSM number if available | DSM756 | NCTC3180 | CCUG2036 | CCUG2037 | CCUG44727 |
|---|---|---|---|---|---|---|
| Bacillus licheniformis | | 1 | 2 | 1 | 0 | 1 |
| Bacillus licheniformis | 17236 | 1 | 1 | 0 | 0 | 0 |
| Bacillus subtilis | 19489 | 0 | 0 | 0 | 1 | 0 |
| Bacillus subtilis | | 0 | 2 | 0 | 0 | 1 |
| Bacillus subtilis | 32324 | 3 | 3 | 3 | 3 | 3 |
| Bacillus subtilis | | 1 | 0 | 1 | 2 | 1 |
| Bacillus subtilis | | 1 | 0 | 0 | 1 | 0 |
| Bacillus subtilis | 32325 | 3 | 3 | 3 | 2 | 3 |
| Bacillus subtilis | 25841 | 2 | 3 | 2 | 2 | 3 |
| Bacillus amyloliquefaciens | 25840 | 2 | 3 | 3 | 2 | 3 |
| Bacillus amyloliquefaciens | 27032 | 3 | 3 | 3 | 2 | 3 |

The results in Tables 1 and 2 of the inhibition of E. coli and Clostridium show that the Bacillus licheniformis strains and many of the Bacillus subtilis strains tested did not demonstrate any E. coli inhibition and poor Clostridium inhibition. However, the two B. subtilis strains DSM32324 and DSM32325 demonstrated impressive results with regard to both E. coli inhibition and Clostridium inhibition.

Example 2

Measurement of Amount of Reducing Sugars in Feed Incubated with a Bacillus Composition The objective of this experiment was to examine the ability of different Bacillus strains to degrade NSP in commercial poultry starter feed and increase the available sugar amount.

TABLE 3

Composition of compound feed used in the assay

| Ingredient | % of feed ration |
|---|---|
| Ground Corn | 30.0 |
| Wheat | 27.0 |
| Soy Bean Meal | 22.5 |
| Rape seed | 6.0 |
| Sunflower | 5.0 |
| Oat | 4.0 |
| Fish meal | 2.0 |
| Limestone | 1.24 |
| Monocalciumfosfat | 0.78 |
| Vegetable oil | 0.54 |
| Sodium bicarbonate | 0.28 |
| Vitamin, mineral, amino acid pre-MIX | 0.25 |
| Sodium chloride (0.17%); | 0.17 |

Compound feed based on wheat-corn-soybean (Table 3) was autoclaved at 121° C. for 15 min for sterilization. Then the feed sample was diluted 20 fold with sodium phosphate buffer to ensure a pH at about 6-6.5 throughout the whole experiment. Bacillus products were obtained by inoculation with 2% overnight culture of the Bacillus strains, grown in Veal Infusion Broth (VIB) (Difco, 234420). A sample was taken for analysis for reducing sugar (DNS) (T=0). After incubation at 37° C. for 24 hours, a sample was taken for CFU determination. Another sample was centrifuged and the supernatant used for determining DNS.

Reducing sugar was analyzed by 3.5-dinitrosalicylic acid (DNS) assay as follows: Na-acetate buffer (100 mM, pH 6)

was mixed with sterile filtered *Bacillus* sample supernatant and incubated at 40° C. for 10 min. DNS reagent was added to the test tube, mixed and incubated in a boiling water bath for 5 min. After cooling, absorbance was measured at 540 nm in a spectrophotometer.

A standard curve was established with a glucose stock solution for presenting results in reducing sugar or enzyme units (amount of enzyme needed to release 1 µmol reducing glucose equivalent in 1 ml per time unit).

The results are shown in Table 4.

Results

TABLE 4

| | Sample DSM number if available | kJ/kg feed |
|---|---|---|
| Control | | 214 |
| Bacillus aryabhattai | | 237 |
| Bacillus licheniformis | 17236 | 340 |
| Bacillus licheniformis | 15326 | 541 |
| Bacillus subtilis | 19489 | 403 |
| Bacillus subtilis | 25841 | 458 |
| Bacillus subtilis | 32325 | 642 |
| Bacillus subtilis | 32324 | 723 |
| Bacillus amyloliquefaciens | 16734 | 515 |
| Bacillus amyloliquefaciens | 27032 | 515 |
| Bacillus amyloliquefaciens | 14623 | 517 |
| Bacillus amyloliquefaciens | 15509 | 853 |
| Bacillus amyloliquefaciens | 25840 | 1142 |
| Bacillus mojavensis | 25839 | 939 |

Table 4 shows the results of a number of different *Bacillus* strains and shows that all *Bacillus* strains tested supplied more nutrients to the animal by delivering more reducing sugars compared to control but also that there is considerable variance between the individual strains.

Based upon the results of *E. coli* and *Clostridium perfringens* inhibition combined with the results of the ability to provide an increased amount of reducing sugars the two best performing strains, the B. subtilis strains DSM32324 and DSM32325, were selected for in vivo studies.

IN VIVO EXAMPLES

Example 3

Efficacy of the *Bacillus Subtilis* Strain DSM32324 in Clostridium Perfringens Challenge in VIVO TRIALS

TABLE 5

| | Diets | | |
|---|---|---|---|
| Ingredient Name % (w/w) | starter | grower | finisher |
| Corn, grain | 58.509 | 64.054 | 69.218 |
| Soybean meal, dehulled, solvent | 35.550 | 29.771 | 24.511 |
| Fat, vegetable | 2.100 | 2.585 | 2.748 |
| Dicalcium phosphate | 1.734 | 1.780 | 1.693 |

TABLE 5-continued

| | Diets | | |
|---|---|---|---|
| Ingredient Name % (w/w) | starter | grower | finisher |
| Calcium carbonate | 1.150 | 0.910 | 0.873 |
| Salt, (NaCl) | 0.386 | 0.390 | 0.393 |

Methionine MHA, L—Lysine, Trace Minerals, Vitamin premix and L-Threonine were included accordingly to the breeder's recommendations.

A non-medicated corn/soya bean meal based diet (Table 5) was used. *Bacillus subtilis* DSM32324 1.2 $10^6$ CFU/g was added to the feed of one of the groups. Feed and water were ad libitum available throughout all trials. All feed was by pen. Starter feed was fed from day 0 to 21. On day 21, non-consumed starter diet was weighed and discarded. Grower feed was fed until day 35 and non-consumed grower feed was weighed and discarded. Likewise, finisher feed was fed until day 42 where non-consumed finisher diet was weighed and discarded.

TABLE 6

| | *Clostridium perfringens* CP-6 | | |
|---|---|---|---|
| Treatment | Inoculation | Pens/Trt | birds/Trt |
| Non-medicated | Not infected | 8 | 320 |
| Non-medicated | Day 19, 20 and 21 | 8 | 320 |
| DSM32324 | Day 19, 20 and 21 | 8 | 320 |

The experiment started with 40 male Ross 308 broiler chickens per pen. The treatments were replicated in eight blocks, randomized within blocks of six pens each.

On Days 19, 20, and 21, all pens, except the non-medicated not infected treatment 1 group, were challenged with a broth culture of C. *perfringens* CP-6 (Knap I, et al., 2010).

This strain is a field isolate of C. *perfringens* known to cause NE originating from a commercial broiler operation and utilized in the present study as the challenge organism. Fresh inoculum was used each day. Each pen received the same amount of inoculum corresponding to approximately $1\times10^8$ to $1\times10^9$ CFU of C. *perfringens* CP-6. The inoculum was administered by mixing into the feed in the base of the tube feeders.

On Day 21, three birds from each pen were selected, sacrificed, group weighed, and examined for the degree of presence of necrotic enteritis lesions. The scoring was based on a 0 to 3 score, with 0 being normal and 3 being the most severe. The scoring was as follows: 0 for normal intestines, 1 for slight mucus covering and loss of tone, 2 for severe necrotizing enteritis, and 3 for extreme necrotizing enteritis with presence of blood in the lumen.

All birds were weighted at day 31, 35 and 42 to see the impact of necrotic enteritis on performance parameters: Means for live weight, average weight gain (AWG), feed consumption, feed conversion ratio (FCR), Necrotic enteritis lesion scores, and mortality (total and NE) were calculated for all pens.

Statistical data analysis was performed in SAS Stat Version 9.2 using ANOVA analysis with complete randomized design to establish differences between treatment groups. Pen was considered the statistical experimental unit with diets as fixed effect. Results were reported as least square means and were assumed different at $P<0.05$.

Results

TABLE 7

| Treatment | FCR | AWG (kg) |
|---|---|---|
| Day 21 | | |
| Non-medicated, not infected | 1.447c | 0.562a |
| Non-medicated, infected | 1.652a | 0.501b |
| DSM32324, infected | 1.575b | 0.567a |
| Day 35 | | |
| Non-medicated, not infected | 1.569b | 1.735ab |
| Non-medicated, infected | 1.634a | 1.679b |
| DSM32324, infected | 1.593b | 1.756a |
| Day 42 | | |
| Non-medicated, not infected | 1.627b | 2.272a |
| Non-medicated, infected | 1.731a | 2.155b |
| DSM32324, infected | 1.645b | 2.303a |

The letters adherent to the results represent treatment groups statistically significantly different from non-medicated control (P 0.05) or from each other.

TABLE 8

| Treatment | NE Lesions scoring | NE % Mortality |
|---|---|---|
| Non-medicated, not infected | 0.05b | 0.0b |
| Non-medicated, infected | 0.58a | 4.3a |
| DSM32324, infected | 0.18b | 0.7b |

The letters adherent to the results represent treatment groups statistically significantly different from non-medicated control (P 0.05) or from each other.

Conclusion

For the performance parameters feed conversion rate (FCR) and average weight gain
(AWG) measured at day 21, day 35 and day 42, a significant improvement was seen for all data points when considering *Bacillus subtilis* DSM3234 as a feed additive compared to the untreated infected control group. Surprisingly, the *Bacillus* treated group did not show any significant differences to the not-infected, non-medicated control group, even though the latter group did not receive the challenge and was considered healthy (Table 7).

With regard to the subclinical enteritis induced in the challenge in vivo trial, the results show that *Bacillus subtilis* DSM3234 decreased necrotic enteritis lesion scoring in chicken and reduced necrotic enteritis mortality significantly (Table 8).

Example 4

Efficacy of the *Bacillus Subtilis* Strain DSM32325 in a *Clostridium Perfringens* Challenge in VIVO TRIALS The study was performed in order to assess the effect of the *Bacillus subtilis* strain DSM32325 on necrotic enteritis frequency and necrotic enteritis lesion scores in chicken.

Male Ross 308 broilers were distributed in three groups with 48 birds per group: infected, untreated control; infected, antibiotic treated group 20 mg amoxicillin/kg body weight; and infected, *Bacillus subtilis* DSM32325 1.2 $10^6$ CFU/g feed treated group.

All animals were fed ad libitum for all phases and were spray vaccinated at arrival in the study facility (D1) against Infectious Bronchitis and against Newcastle Disease. Until D9, the birds were fed a starter feed "Kip 1-3" purchased at a commercial feed mill (Cibus, Kaaistraat 49; 8800 Roeselare, Belgium). The quantitative composition of the starter feed was the same for all animals except for the inclusion of the corresponding product in each group. From D9 until D26, the birds received a grower feed with high protein content and fish meal included at 40%. The grower feed "Teler2" was purchased from a commercial feed mill (Cibus, Kaaistraat 49; 8800 Roeselare, Belgium). The composition of the grower feed for the different treatment groups was exactly the same, except for the inclusion of the corresponding product in each group. The feeds received a group code and the treatment premix was subsequently mixed with the amount of feed aimed for each feed batch.

On day 19, 20, 21 and 22, approximately $10^9$ CFU *Clostridium perfringens* strain 56 (Timbermont et al. 2009) were orally administered three times per day to all birds as described in Timbermont et al. 2009. Necrotic enteritis lesions were determined on day 25 and 26 (0-6 score) (Johnson & Reid 1970). The frequency of NE and NE scores was analyzed using logistic and linear regression models, respectively. Statistical significance was assessed at P≤0.05.

Results

The percentage of birds positive to macroscopic necrotic enteritis lesions (lesion score 2) on each sampling day is presented in the table below. For each day, a linear regression model was fit to analyze differences between the treatment groups and the IUC. An additional model was fit with the data of Day 25 and Day 26 combined. In this model, Day 25 and 26 and Group were added as fixed effect.

TABLE 9

| | Day 25 | Day 26 | Day 25 and 26 | |
|---|---|---|---|---|
| Group | % NE | % NE | % NE | P ≤ 0.05 |
| Infected Untreated Control | 50 | 23 | 36.5 | ref. |
| Amoxicillin | 44 | 14 | 29 | |
| *Bacillus subtilis* DSM32325 | 25 | 7 | 16 | ** |

** marked numbers represent treatment groups statistically significantly different from untreated control IUC (P ≤ 0.05).

Mean NE scores by group and day were calculated in a similar manner.

TABLE 10

| | Day 25 | Day 26 | Day 25 and 26 | |
|---|---|---|---|---|
| Group | Mean score | Mean score | Mean score | P ≤ 0.05 |
| Infected Untreated Control | 1.75 | 1.15 | 1.450 | Ref |
| Amoxicillin | 1.56 | 1.07 | 1.315 | |
| *Bacillus subtilis* DSM32325 | 1.25 | 1.00 | 1.125 | ** |

** marked numbers represent treatment groups statistically significantly different from untreated control IUC (P ≤ 0.05).

The results show that *Bacillus subtilis* DSM32325 decreased necrotic enteritis frequency in chicken compared to infected untreated control in a statistically significant manner when the data of Day 25 and 26 were combined.

Surprisingly, the necrotic enteritis frequency was even lower in the *Bacillus* treated group than in the Amoxicilin treated group (Table 9).

Further, *Bacillus subtilis* DSM32325 reduced necrotic enteritis severity (mean score) compared to infected untreated control in a statistically significant manner when the data of Day 25 and 26 were combined. Surprisingly, the mean score was even lower in the 5 *Bacillus* treated group than in the Amoxicilin treated group (Table 10).

Example 5

Performance Feeding Trial

Animals:

One day old Ross 308 male broilers were allocated at random to 72 floor-pens, each containing 25 chickens in each pen such that each treatment was replicated 12 times. Experimental groups were negative control (NC), *Bacillus subtilis* DSM19489, *Bacillus subtilis* DSM32324 and *Bacillus subtilis* DSM32325.

Diets:

Three phase mash feeds (from 1 to 14 days, 15 to 28 days and 29 to 42 days) free from any antibiotic compounds, inhibitory, performance enhancers, other probiotics, enzymes or acidifiers were provided ad libitum. Diets were based on maize, wheat, barley, rye and soybean meal.

TABLE 11

Composition content of the basal diets

| INGREDIENTS, % | Starter 0-14 d | Grower 15-28 d | Finisher 29-42 d |
|---|---|---|---|
| Maize | 19.647 | 19.574 | 20.207 |
| Soybean meal 44% CP | 30.147 | 24.190 | 20.210 |
| Wheat | 15.000 | 15.000 | 15.000 |
| Fullfat soybean | 12.000 | 15.000 | 15.000 |
| Barley | 10.000 | 10.000 | 10.000 |
| Rye | 5.000 | 7.5000 | 10.000 |
| Soy oil | 4.141 | 4.833 | — |
| Animal fat (lard) | — | — | 5.905 |
| Calcium carbonate | 1.139 | 1.067 | 1.045 |
| Monocalcium phosphate | 1.546 | 0.462 | 1.286 |
| Salt | 0.327 | 0.302 | 0.303 |
| Sodium bicarbonate | 0.100 | 0.100 | 0.100 |
| DL-Methionine | 0.295 | 0.326 | 0.289 |
| L-Lysine HCl | 0.186 | 0.168 | 0.176 |
| L-Threonine | 0.071 | 0.077 | 0.078 |
| Vit&Min Premix | 0.400 | 0.400 | 0.400 |

Test Articles

The test articles *Bacillus subtilis* DSM19489, *Bacillus subtilis* DSM32324, and *Bacillus subtilis* DSM32325 were fed throughout the duration of the 42-day trial in a dosage of $1.210^6$ CFU/g feed.

Observations

Average daily gain (ADG), body weight (BW), feed intake as average daily feed intake (ADFI) and feed efficiency; feed conversion ratio (FCR) at 1, 14, 28, 35 and 42 days of age were measured. General health, medical treatment and mortality were evaluated daily. European production efficiency factor (EPEF) was calculated: [(liveability, % ×BW 15 gain, kg)/(Study duration in days× FCR)]×100.

Statistical Analysis and Interpretation

Analysis of Variance was the basic statistical technique applied. The data were analysed as a completely randomised design by GLM of SPSS v. 19.0 followed by Tukey's mean test. $P<0.05$ was considered a statistically significant difference, while $0.05<P<0.10$ was considered a near-significant trend.

Results

The health of the animals was considered normal throughout the study, and no adverse events were noted. There were 23 deaths/culls (1.27%) between 0 and 14 days, 19 deaths/culls (1.07%) between 14 and 28 days and 16 deaths/culls (0.91%) between 28 and 42 days, and they were not related to treatment. Total mortality/cull ratio of 58/1800 birds (3.22%) at 42 days was considered normal.

TABLE 12

| | Treatment | Whole fattening phase, 0-42 d | | | |
|---|---|---|---|---|---|
| | | ADG, g/d | ADFI, g/d | FCR | EPEF |
| 1 | Negative control | $68.6^b$ | 116.2 | $1.69^b$ | $386^b$ |
| 2 | DSM19489 (*B. subtilis*) | $70.4^{ab}$ | 116.1 | $1.65^a$ | $420^a$ |
| 3 | DSM32324 (*B. subtilis*) | $71.9^a$ | 116.6 | $1.62^a$ | $424^a$ |
| 5 | DSM32325 (*B. subtilis*) | $70.9^a$ | 115.9 | $1.64^a$ | $416^a$ |
| | SEM (n = 12) | 0.53 | 0.79 | 0.006 | 5.3 |
| | P (Probability) | 0.0002 | 0.7429 | <0.0001 | <0.0001 |

The performance of the animals was in accordance with trial conditions (male broilers fed mash diets and raised in floor pens). At 28 days of age, broilers receiving DMS32324 were 3.77% heavier than control birds (P<0.05). At 35 and 42 days of age, broilers supplemented with the Bacilli strains DSM32324 or DSM32325 were significantly heavier than control animals, showing the DSM19489 broiler group as having intermediate weights. During the starter period (from 0 to 14 days of age), no significant differences between treatments were observed in growth, feed intake or feed conversion. During the grower period (from 15 to 28 days of age), chickens receiving DSM32324 grew significantly more than control broilers. The feed conversion of all broilers supplemented with probiotics was significantly improved when compared to control animals. No significant differences between treatments were observed in growth, feed intake or feed conversion during the last week of trial (from 35 to 42 days of age).

For the global fattening period (0-42 days of age), broilers supplemented with the Bacilli strains DSM32324 or DSM32325 grew significantly more than control animals. The feed conversion (FCR) and EPEF of all broilers supplemented with probiotics were significantly improved when compared to those of the control animals.

Example 6

Performance Feeding Trial

The objective of this study was to evaluate the addition of the *Bacillus subtilis* DSM32324 and commercial product Bacillus subtilis DSM19489 in broiler diets. The aim was to evaluate the effect of the products on production parameters in a wheat-based diet including coccidiostats and feeding enzymes.

There were 1300 day old chicks (males) of ROSS 308 in each treatment—divided in 10 pens of 130 chicks. Chickens were fed ad libitum with a three-phase feed in pelleted form in all phases and drinking water was supplied ad libitum by nipple drinkers. The composition of the diets is shown in the table below. The feed was supplied by Mezinárodní testování drůbeže, s.p., feed mill Lysá nad Labem.

Probiotic Feed Additives were Distributed as follows

T1: Un-supplemented control group;
T2: *Bacillus subtilis* DSM19489 $1.2 \times 10^6$ CFU/g feed;
T3: *Bacillus subtilis* DSM32324 $1.2 \times 10^6$ CFU/g feed.

TABLE 13

Diet formulas

| Components | Starter diet Day 1-13 | Grower diet Day 14-28 | Finisher diet Day 29-42 |
|---|---|---|---|
| Wheat | 40.000 | 51.880 | 56.450 |
| Maize | 19.460 | 10.000 | 10.000 |
| Extr. soybean meal | 32.800 | 29.500 | 24.600 |
| Soybean oil | 4.000 | 5.000 | 5.800 |
| L-lysine HCl | 0.170 | 0.220 | 0.200 |
| DL-methionine | 0.060 | 0.100 | 0.120 |
| L-threonine | 0.060 | 0.080 | 0.060 |
| Limestone | 1.500 | 1.500 | 1.400 |
| Salt | 0.250 | 0.250 | 0.240 |
| Monocalcium phosphate | 1.000 | 0.770 | 0.500 |
| Soda bicarbonate | 0.200 | 0.200 | 0.130 |
| AMV BR1 Plus | 0.500 | — | — |
| AMV BR2 Plus | — | 0.500 | — |
| AMV BR3 Plus | — | — | 0.500 |

Live weight was measured on days 1 (all the birds in each pen were weighed altogether), 13 and 28 (all birds were weighed individually, without fasting) and 42 (all the birds were weighed individually after 12 hours of fasting).

Feed consumption per 1 kg of live weight was recorded per pen on days 13, 28 and 42 and the feed conversion ratio was calculated.

Statistical Analyses

Performance results of live weight on day 13, 28 and 42 and mortality were statistically evaluated using the one-factorial ANOVA model main effect of treatment Dunnett test (all supplemented diets against un-supplemented Control (T1)).

Results

The Coefficient of variation (CV) for Feed Conversion and Feed Conversion Ratio averaged 2.7%. CV for final Body Weight and Body Weight gain was 3.7%, and treatment average of within pen variation of final BW (as a measure for flock homogeneity) ranged from 10.3 to 15.3%.

Mortality in the flocks was low (overall 3.4% in un-supplemented birds) and surprisingly low for the first 13 days.

TABLE 14

| | Mortality in the period | | | | | | | |
|---|---|---|---|---|---|---|---|---|
| | Day 1-13 | | Day 14-28 | | Day 29-42 | | Day 1-42 | | |
| Treatment | No of birds | G | No of birds | g | No of birds | g | No of birds | g | % |
| Unsupplemented | 2 | 514 | 18 | 14421 | 24 | 45212 | 44 | 60147 | 3.38 |
| DSM19489 | 4 | 1459 | 10 | 7074 | 14 | 25049 | 28 | 33582 | 2.15 |
| DSM32324 | 3 | 1048 | 14 | 11295 | 7 | 11473 | 24 | 23816 | 1.85 |

Conclusion

DSM19489 had a tendency of reduced mortality (p=0.096) and *Bacillus subtilis* DSM32324 had a marked and significantly reduced mortality in especially the finisher period which also served for statistical significance of mortality for the overall trial.

Example 7

Effect of different *Bacillus* Strains on Growth Performance, Digestibility and Gut Health in Broilers The birds were housed per 15 animals in pens measuring 1.2 m×0.8 m from D1 until the end of the trial (D42). The floor in each pen was covered with wood shavings in a thickness of about 5 cm. One commercial pan feeder with a feed reservoir was suspended on the inside of the pen and four drinking nipples were mounted on the side of the pen.

The birds were fed a suboptimal diet with rye included as a source of non-starch proteins and no feed enzymes. Until D22, the birds were fed a starter feed. From D22 until D42, the birds were fed a grower feed. The quantitative composition of the feed was the same for all animals except for the inclusion of the corresponding strain in each group. Details on the feed composition are shown in Table 15. The strains to be tested (DSM32324, DSM25840 and DSM32325 were mixed at a ratio of $1.2 \times 10^6$ CFU/ gram feed into the feed.

TABLE 15

Composition content of the basal diets

| INGREDIENTS, % | Starter 0-21 d | Finisher 22-42 d |
|---|---|---|
| Maize | 41.6 | 31.6 |
| Soybean meal 47.3% CP | 26.0 | 24.0 |
| Rapeseed meal 32.5 CP | 4.0 | 5.0 |
| Fish meal 70.0 CP | 2.0 | — |
| Wheat | 15.0 | 20.0 |
| Rye | 5.0 | 10.0 |
| Soy oil | 1.0 | 1.0 |
| Animal fat (lard) | 1.5 | 5.0 |
| Calcium carbonate | 1.359 | 1.10 |
| Monocalcium phosphate | 1.2 | 0.85 |
| Salt | 0.18 | 0.21 |
| Sodium bicarbonate | 0.27 | 0.23 |
| DL-Methionine | 0.195 | 0.195 |
| L-Lysine HCl | 0.15 | 0.21 |
| L-Threonine | 0.045 | 0.065 |
| L-valine | 0.015 | 0.035 |
| Vit&Min Premix | 0.500 | 0.500 |

At set-up (D1), 960 animals were placed in 64 pens (i.e. 15 animals per pen). As mentioned above, a starter feed was administered to all birds from D1 until D22. From D22 until D42, a grower feed was administered to all birds.

On D12, D22 and D42, tissue samples were taken from the duodenum, jejunum and ileum of 1 bird per pen.

On D1, D12, D22, D33 and D42, birds and feed were weighted to analyse effects of the probiotics on the growth performance (weight gain, feed intake and feed conversion) during the different periods.

On D22 and D42, 6 birds per pen were euthanized. The ileal and caecal content were pooled per pen. Additional samples of the ileal and caecal content were frozen and stored at −80° C.

On D19-D22 and D40-42, 3 faecal droplings per pen were collected daily. The faeces were pooled per pen.

Health was recorded on a daily basis. From D1 until the end of the study at D42, general health observations were made and recorded by experienced stock personnel on a daily basis. If the animals showed signs of illness, general health observations were made at least twice daily. Mortalities were recorded on a daily basis.

Body weight (BW) was measured per pen on D1. The animal BW weight was measured individually on D12, D22, D33 and D42. Daily weight gain (DWG) was calculated per pen for the periods D1 till D12, D1 till D22, and D1 till D42. Daily weight gain (DWG) was calculated per animal for the periods D12 to D22, D22 to D33, D33 to D42 and D22 to D42.

The difference in BW between the start and the end of each study period was the weight gain (WG) for that period. The daily weight gain (DWG) was calculated as the WG divided by the number of days in the corresponding period. The DWG of the dead animals was included when calculating the average DWG of each group, considering the date of death of the bird as the end of the study period for that bird.

Daily Feed Consumption (FC) and Feed conversion ratio (FCR) were calculated at pen level for the periods D1 to D12, D12 to D22, D1 to D22, D22 to D33, D33 to D42, D22 to D42 and D1 to D42.

The feed provided to the animals ("Feed IN") was weighed on D1, D12, D22 and D33. When on any other day a pen was running out of feed and more feed was needed to be provided, the added feed was also weighed and recorded as "Feed IN". The remaining feed in each pen ("Feed OUT") was weighed on D12, D22, D33 and D42. The difference in feed weight at the start and the end of each study period was calculated to define the feed consumption (FC) per pen. The difference in feed weight between the start and the end of each study period ("Feed IN"-"Feed OUT") was the FC of the corresponding pen for that period. The average daily FC per bird was calculated as the FC divided by the number of days in the corresponding period multiplied by the number of animals that would have eaten during that period in the corresponding pen.

The dry matter, crude protein, crude fat, Ca, P, energy and titanium dioxide content were determined on the pooled ileal and caecal content collected on D22 and D42 and on the feed. Titanium oxide was added to the feed (0.3%) as an inert marker. The apparent ileal digestibility was calculated as described by Waititu et al., 2014.

Samples were analysed at the Department of Animal Sciences, Subdivision Animal Nutrition of Wageningen University under the supervision of Leon de Jonge. The following methods were used:

Dry matter: 3h drying at 103° C. based on ISO 6496 (1999)

Ash: 3h heating at 550° C. based on ISO 5984 (2002)

Protein: Kjeldahl method based on ISO 5983 (2005)

Fat: Extraction with petroleum ether after treatment with acid based on ISO 6492 (1999)

Calcium: Absorption spectroscopy based on ISO 6869 (2000)

Phosphorus: Spectrometric determination based on ISO 6869 (2000)

Energy: bomb caloric method based on ISO 9831 (1998)

Titanium: spectrometric determination based on Kjeldahl destruction followed by coloring with peroxide and absorption measurement at 408 nm The dry matter, crude protein, crude fat, Ca, energy and titanium dioxide content was determined on the pooled faeces collected on D19-D22 and D40-D42 and the feed. Titanium oxide was added to the feed (0.3%) as an inert marker. The total tract apparent retention was calculated as described by Waititu et al., 2014.

Data was analysed with RStudio (Version 0.99.467, RStudio, Inc.). All data except body weight and daily weight gain at bird level were analysed using linear regression models with treatment group as fixed effect (procedure lm of the core package). Body weight and daily weight gain at bird level were analysed using linear mixed regression models with treatment group as fixed effect and pen as random effect to correct for the clustering of birds within pens (procedure lme of the package nlme) (Protocol deviation n° 1). Statistical significance was assessed at $P \leq 0.05$.

Results

Eight birds died during the study (0.8%).

The table below shows the mean body weight per study day and treatment. The differences were analyzed with linear mixed regression models with treatment as categorical fixed effect and pen as random effect to account for the clustering of birds within pens.

TABLE 16

| | Mean body weight | | | | | | | |
|---|---|---|---|---|---|---|---|---|
| | D 12 | | D 22 | | D 33 | | D 42 | |
| Group name | Mean | P-value | Mean | P-value | Mean | P-value | Mean | P-value |
| NC | 266 | Ref. | 687 | Ref. | 1569 | Ref. | 2390 | Ref. |
| DSM32324 | 272 | 0.220 | 730 | 0.010 | 1613 | 0.208 | 2459 | 0.176 |
| DSM25840 | 286 | <0.001 | 759 | <0.001 | 1672 | 0.003 | 2525 | 0.009 |
| DSM32325 | 283 | 0.001 | 744 | 0.001 | 1632 | 0.070 | 2476 | 0.087 |

Table 17 shows the mean apparent ileal digestibility (AID) per nutrient and treatment. The differences were analyzed with linear regression models with treatment as categorical fixed effect (procedure lm of the core package).

TABLE 17

| | Mean apparent ileal digestibility (AID) | | | | | | | | | | | | | |
|---|---|---|---|---|---|---|---|---|---|---|---|---|---|---|
| | Dry matter | | Ash | | Protein | | Fat | | Ca | | Phosphorus | | Energy | |
| Group name | Mean | P-value | Mean | P-value | Mean | P-value | Mean | P-value | Mean | P-value | Mean | P-value | Mean | P-value |
| NC | 57.6 | Ref. | 38.2 | Ref. | 74.1 | Ref. | 61.6 | Ref. | 36.6 | Ref. | 53.8 | Ref. | 65.0 | Ref. |
| DSM32324 | 58.8 | 0.233 | 38.7 | 0.697 | 76.3 | 0.050 | 59.5 | 0.515 | 36.3 | 0.900 | 53.6 | 0.879 | 66.5 | 0.160 |
| DSM25840 | 59.5 | 0.075 | 40.8 | 0.039 | 76.3 | 0.050 | 64.0 | 0.458 | 33.4 | 0.190 | 54.0 | 0.842 | 67.2 | 0.043 |
| DSM32325 | 57.4 | 0.862 | 37.5 | 0.568 | 74.6 | 0.639 | 63.1 | 0.640 | 31.3 | 0.031 | 51.0 | 0.039 | 65.4 | 0.677 |

Conclusion

The objective of this study was to evaluate the effect of different *Bacillus* strains on growth performance and digestibility in broilers.

The strains tested showed significant effects on performance and apparent ileal digestibility:

Birds supplemented with DSM32324 showed a higher daily weight gain (Table 16), daily feed intake and feed conversion ratio in the starter period (data not shown) and a higher protein digestibility at D42 (Table 17) compared to non-supplemented birds.

Birds supplemented with DSM25840 showed a higher daily weight gain (Table 16) and daily feed intake in the starter period (data not shown), a higher body weight at D42 15 (Table 16) and a higher ash, protein and energy digestibility at D42 (Table 17) compared to non-supplemented birds.

Birds supplemented with DSM32325 showed a higher daily weight gain (Table 16) and daily feed intake in the starter period (data not shown), and a lower Ca and Phosphorus digestibility at D42 (Table 17) compared to non-supplemented birds.

In conclusion, all three strains showed surprisingly good and significantly improved results.

Example 8

Comparative Efficacy of 4 Diffent Probiotics Administered in the Feed for the Control of Necrotic Enteritis caused by Clostridium Perfringens in Broiler Chickens The objective of the study was to evaluate the effect of DSM32324, DSM25840 and DSM32325 as well as a composition of all of them in a ratio of 8:3:5, EPB5, on performance of Cobb 500 broilers challenged with NE and to compare the effect of each strain with the effect of the composition.

Day of hatch Cobb 500 male chicks were obtained from Cobb Vantress hatchery, Cleveland, Ga. 2250 chicks were allocated to the study. All birds were spray vaccinated with coccidia vaccine with the label recommended dosage on day of hatch.

Standard floor pen management practices were used throughout the experiment. Pens were checked daily for mortality. Bird weights (kg) by pen were recorded at study initiation and DOTs 21,35, and 42.

Broiler diets were fed as crumbles (starter feed) or as pellets (grower and finisher). The quantitative composition of the feed was the same for all animals except for the inclusion of the *Bacillus* strains or composition for the treatment groups. Diet formulations:

TABLE 18

| Ingredient Name % (w/w) | starter | grower | finisher |
|---|---|---|---|
| Corn, grain | 58.509 | 64.054 | 69.218 |
| Soybean meal, dehulled, solvent | 35.550 | 29.771 | 24.511 |
| Fat, vegetable | 2.100 | 2.585 | 2.748 |
| Dicalcium phosphate | 1.734 | 1.780 | 1.693 |
| Calcium carbonate | 1.150 | 0.910 | 0.873 |
| Salt, (NaCl) | 0.386 | 0.390 | 0.393 |

Methionine MHA, L - Lysine, Trace Minerals, Vitamin premix and L-Threonine were included accordingly to the breeder's recommendations.

All feed was by pen. Starter feed was issued and fed from DOT 0 to 21. On DOT 21, non-consumed starter was weighed and discarded. Grower feed was issued and fed until DOT On DOT 35, non-consumed grower was weighed and discarded. Finisher feed was issued and fed until DOT 42. On DOT 42, non-consumed finisher was weighed and discarded.

The experiment consisted of 45 pens starting with 50 male broiler chickens per pen. The treatments were replicated in nine blocks, randomized within blocks of five pens each.

TABLE 19

| Treatment | Description | Feed Target (cfu/g feed) | Clostridium perfringens | Pens/Trt |
|---|---|---|---|---|
| T1 | Control without probiotic | 0 | DOT 19, 20, and 21 | 9 |
| T2 | Bacillus subtilis DSM32324 | $8 \times 10^5$ | DOT 19, 20, and 21 | 9 |
| T3 | Bacillus subtilis DSM32325 | $5 \times 10^5$ | DOT 19, 20, and 21 | 9 |
| T4 | Bacillus amyloliquefaciens DSM25840 | $3 \times 10^5$ | DOT 19, 20, and 21 | 9 |
| T5 | EBP5 | $1.6 \times 10^6$ | DOT 19, 20, and 21 | 9 |

On Days 19, 20, and 21 all pens were challenged with a broth culture of C. perfringens. A field isolate of C. perfringens known to cause NE was utilized as the challenge organism. Fresh inoculum was used each day. The titration levels were approximately $10^{8-9}$ CFU/pen. Each pen received the same amount of inoculum. The inoculum was administered by mixing into the feed in the base of the tube feeders.

On Day 21, five birds from each pen were selected, sacrificed, group weighed, and examined for the degree of presence of Necrotic Enteritis lesions. The scoring was based on a 0 to 3 score, with 0 being normal and 3 being the most severe. The scoring was as follows: 0 for normal intestines, 1 for slight mucus covering and loss of tone, 2 for severe necrotizing enteritis, and 3 for extreme necrotizing enteritis with presence of blood in the lumen.

No concomitant drug therapy was used during the study. Pen was used as the statistical unit. Means for live weight, weight gain, feed consumption, feed conversion ratio (FCR), NE lesion scores, and mortality (total and NE) were calculated. The raw data were analyzed statistically (ANOVA) using a Random Complete Block Design. Tukey's HSD test ($p \le 0.05$) was used to separate means when ANOVA F values are significant ($p \le 0.05$). Different superscripts within lines indicate levels of significance at $P<0.05$.

Results

TABLE 20

Day 21

| | Treatment | Feed Intake | FCR | AWG (kg) |
|---|---|---|---|---|
| 1. | Non-medicated | 44.70a | 1.903a | 0.430b |
| 2. | Bacillus subtilis DSM32324 | 43.48a | 1.694c | 0.476a |
| 3. | Bacillus subtilis DSM32325 | 44.92a | 1.649c | 0.509a |
| 4. | Bacillus amyloliquefaciens DSM25840 | 42.32a | 1.786b | 0.436b |
| 5. | EBP5 | 43.14a | 1.646c | 0.488a |

TABLE 21

Day 35

| | Treatment | Feed Intake | FCR | AWG (kg) |
|---|---|---|---|---|
| 1. | Non-medicated | 143.17a | 1.909a | 1.606b |
| 2. | Bacillus subtilis DSM3234 | 141.29a | 1.802b | 1.667a |
| 3. | Bacillus subtilis DSM3235 | 145.73a | 1.816b | 1.695a |
| 4. | Bacillus amyloliquefaciens DSM25840 | 140.13a | 1.801b | 1.641ab |
| 5. | EBP5 | 142.33a | 1.774b | 1.689a |

TABLE 22

Day 42

| | Treatment | Feed Intake | FCR | AWG. (kg) | Percent Mortality |
|---|---|---|---|---|---|
| 1. | Non-medicated | 199.77a | 1.957a | 2.237b | 4.2a |
| 2. | Bacillus subtilis DSM32234 | 197.67a | 1.873bc | 2.291ab | 3.1a |
| 3. | Bacillus subtilis DSM32235 | 203.61a | 1.896b | 2.322a | 2.7a |
| 4. | Bacillus amyloliquefaciens DSM25840 | 196.86a | 1.898b | 2.244b | 3.3a |
| 5. | EBP5 | 199.87a | 1.841c | 2.342a | 2.7a |

TABLE 23

| | Treatment | NE Lesions | NE % Mortality |
|---|---|---|---|
| 1. | Non-medicated | 1.0a | 4.2a |
| 2. | Bacillus subtilis DSM32234 | 0.5c | 0.4b |
| 3. | Bacillus subtilis DSM32235 | 0.5c | 0.9b |
| 4. | Bacillus amyloliquefaciens DSM25840 | 0.7b | 1.6b |
| 5. | EBP5 | 0.5c | 0.4b |

Discussion and Conclusion

For the performance parameters feed conversion rate (FCR) and average weight gain (AWG) measured at day 21, day 35 and day 42, a significant improvement was seen for all data points when considering single strain probiotic feed additives and EBP5 in particular compared to the untreated infected control group.

Surprisingly, EBP5 treated groups showed significant improvement for some of the performance parameters compared to the groups with the Bacillus single strain treatment which again showed significant differences in performance parameters to the non-medicated infected control group.

With regard to the subclinical enteritis induced in the challenge in vivo trial, the results show that both the single strains Bacillus subtilis DSM32234, Bacillus subtilis DSM32235 and Bacillus amyloliquefaciens DSM25840 as well as the combination EBP5 decreased necrotic enteritis lesion scoring in chicken and reduced necrotic enteritis mortality significantly.

Example 9

A Bacillus Composition with Three Bacillus Strains in Male Turkeys

The trial consisted of 300 one-day old healthy male turkey chickens (Kartzfehn Premium) which were allocated at random to 60 pens with 5 birds per pen (10 repetitions per any treatment group).

Diets consisted of unmedicated commercial-type turkey diet having an ingredient composition as outlined in table 24 for turkeys from d 01 to d 63 and in table 25 for turkeys from d 64 to d 147 of age. The quantitative composition of the feed was the same for all animals except for the inclusion of the Bacillus composition for the treatment group.

The Bacillus composition EBP5 comprising $1.6 \times 10^9$ CFU/g of DSM32324, $0.6 \times 10^9$ CFU/g of DSM25840 and $1.0 \times 10^9$ CFU/g of DSM32325, i.e. in a ratio of 8:3:5, was mixed into the feed.

TABLE 24

Ingredient composition in diets P1, P2, and P3 for turkeys

| Feeding phase | | P1 (d 01 to 14 of age) | P2 (d 15 to 35 of age) Ingredients | P3 (d 36 to 63 of age) |
|---|---|---|---|---|
| Soybean meal (Crude Protein: 49%) | g/kg | 470.00 | 442.80 | 369.00 |
| Corn | g/kg | 352.40 | 389.40 | 455.70 |
| Wheat | g/kg | 79.30 | 79.30 | 79.30 |
| Soybean oil | g/kg | 35.00 | 35.00 | 41.00 |
| Monocalcium phosphate | g/kg | 25.00 | 17.90 | 17.90 |
| Limestone | g/kg | 20.20 | 17.80 | 18.80 |
| Premix *) | g/kg | 12.00 | 12.00 | 12.00 |
| Methionine | g/kg | 2.50 | 2.20 | 2.20 |
| Lysine | g/kg | 1.60 | 1.60 | 2.10 |
| Limestone | g/kg | 2.00; 1.90; 1.75; 1.50; 1.00; 0 | 2.00; 1.90; 1.75; 1.50; 1.00; 0 | 2.00; 1.90; 1.75; 1.50; 1.00; 0 |
| EPB5 | g/kg | 0; 0.1; 0.25; 0.50; 1.00; 2.00 | 0; 0.1; 0.25; 0.50; 1.00; 2.00 | 0; 0.1; 0.25; 0.50; 1.00; 2.00 |

*) Contents per kg Premix: 600000 I.U. Vit. A (acetate); 120000 I.U. Vit. D3; 6000 mg Vit. E (α-tocopherol acetate); 200 mg Vit. K3 (MSB); 250 mg Vit. B1 (mononitrate); 420 mg Vit. B2 (cryst. riboflavin); 300 mg Vit. B6 (pyridoxin-HCl); 1500 µg Vit. B12; 3000 mg niacin (niacinamide); 12500 µg biotin (commercial, feed grade); 100 mg folic acid (cryst., commercial, feed grade); 1000 mg pantothenic acid (Ca d-pantothenate); 60000 mg choline (chloride); 5000 mg iron (iron carbonate); 5000 mg zinc (zinc sulfate); 6000 mg manganese (manganous oxide); 1000 mg copper (copper oxide); 45 mg iodine (calcium-iodate); 20 mg selenium (sodium-selenite); 140 g sodium (NaCl); 55 g magnesium (magnesium sulfate); carrier: calcium carbonate (calcium min 38%); Monteban G100: 5'833 mg

TABLE 25

Ingredient composition in diets P4, P5, and P6 for turkeys

| Feeding phase | | P4 (d 64 to 91 of age) | P5 (d 92 to 119 of age) Ingredients | P6 (d 120 to 147 of age) |
|---|---|---|---|---|
| Corn | g/kg | 524.60 | 606.80 | 658.00 |
| Soybean meal (Crude Protein: 49%) | g/kg | 303.00 | 225.00 | 173.00 |
| Wheat | g/kg | 79.30 | 79.30 | 79.30 |
| Soybean oil | g/kg | 37.80 | 35.00 | 38.00 |
| Monocalcium phosphate | g/kg | 19.00 | 16.00 | 14.90 |
| Limestone | g/kg | 18.70 | 17.00 | 15.30 |
| Premix * | g/kg | 12.00 | 12.00 | 12.00 |
| L-Lysine | g/kg | 2.00 | 2.80 | 3.50 |
| DL-Methionine | g/kg | 1.60 | 1.50 | 1.50 |
| L-Threonine | g/kg |  | 0.50 | 0.30 |
| L-Tryptophan | g/kg |  | 0.10 | 0.20 |
| Limestone | g/kg | 2.00; 1.90; 1.75; 1.50; 1.00; 0 | 2.00; 1.90; 1.75; 1.50; 1.00; 0 | 2.00; 1.90; 1.75; 1.50; 1.00; 0 |
| Probiotic | g/kg | 0; 0.1; 0.25; 0.50; 1.00; 2.00 | 0; 0.1; 0.25; 0.50; 1.00; 2.00 | 0; 0.1; 0.25; 0.50; 1.00; 2.00 |

* Contents per kg Premix: 600000 I.U. Vit. A (acetate); 120000 I.U. Vit. D3; 6000 mg Vit. E (α-tocopherol acetate); 200 mg Vit. K3 (MSB); 250 mg Vit. B1 (mononitrate); 420 mg Vit. B2 (cryst. riboflavin); 300 mg Vit. B6 (pyridoxin-HCl); 1500 µg Vit. B12; 3000 mg niacin (niacinamide); 12500 µg biotin (commercial, feed grade); 100 mg folic acid (cryst., commercial, feed grade); 1000 mg pantothenic acid (Ca d-pantothenate); 60000 mg choline (chloride); 5000 mg iron (iron carbonate); 5000 mg zinc (zinc sulfate); 6000 mg manganese (manganous oxide); 1000 mg copper (copper oxide); 45 mg iodine (calcium-iodate); 20 mg selenium (sodium-selenite); 140 g sodium (NaCl); 55 g magnesium (magnesium sulfate); carrier: calcium carbonate (calcium min 38%); Monteban G100: 5'833 mg

TABLE 26

Effect of EBP5 on performance in male turkeys during the overall feeding period (P1 to P6)

| | | T1 | T2 | T3 | T4 | T5 | T6 | P value |
|---|---|---|---|---|---|---|---|---|
| Total birds | no | 50 | 50 | 50 | 50 | 50 | 50 | |
| Repetitions | no | 10 | 10 | 10 | 10 | 10 | 10 | |
| EBP5 | mg/kg | | 100 | 250 | 500 | 1,000 | 2,000 | |
| P 1 to P 6 (d 01 to d 147 of age) | | | | | | | | |
| Birds | no | 48 | 49 | 48 | 48 | 49 | 49 | |
| Body weight start | g | 61.2 ± 1.0 | 61.2 ± 0.8 | 61.3 ± 1.0 | 61.2 ± 1.0 | 61.3 ± 0.8 | 61.2 ± 1.0 | 1.000 |
| Body weight end | g | 24169.3 ± 321.6$^a$ | 24522.9 ± 335.0$^{ab}$ | 24721.4 ± 252.2$^{bc}$ | 24917.7 ± 251.2$^c$ | 25333.3 ± 311.2$^d$ | 25759.3 ± 282.2$^e$ | <0.001 |
| Body weight gain | g | 24108.1 ± 320.9$^a$ | 24461.7 ± 334.6$^{ab}$ | 24660.2 ± 252.0$^{bc}$ | 24856.5 ± 251.1$^c$ | 25272.0 ± 310.9$^d$ | 25698.1 ± 282.4$^e$ | <0.001 |
| Body weight gain/d | g/d | 164.0 ± 2.2$^a$ | 166.4 ± 2.3$^{ab}$ | 167.8 ± 1.7$^{bc}$ | 169.1 ± 1.7$^c$ | 171.9 ± 2.1$^d$ | 174.8 ± 1.9$^e$ | <0.001 |
| Feed intake | g | 51538.2 ± 735.3$^{ab}$ | 51309.4 ± 408.7$^{ab}$ | 51294.0 ± 377.0$^{ab}$ | 50941.6 ± 598.1$^{ab}$ | 51049.7 ± 404.7$^{ab}$ | 51737.8 ± 581.9$^b$ | 0.016 |
| Feed intake/d | g/d | 350.6 ± 5.0$^{ab}$ | 349.0 ± 2.8$^{ab}$ | 348.9 ± 2.6$^{ab}$ | 346.5 ± 4.1$^{ab}$ | 347.3 ± 2.8$^a$ | 352.0 ± 4.0$^b$ | 0.016 |
| Feed conversion | | 2.138 ± 0.024$^d$ | 2.098 ± 0.035$^c$ | 2.080 ± 0.026$^{bc}$ | 2.050 ± 0.025$^{ab}$ | 2.020 ± 0.032$^a$ | 2.013 ± 0.025$^a$ | <0.001 |

$^{ab}$Different superscripts within lines indicate levels of significance at P < 0.05

Body Weight Gain

The initial body weight of turkey chickens was at around 61.2 g and nearly similar in all treatment groups. The overall body weight gain in turkeys fed diets without containing EBP5 (control group) amounted to 24.11 kg; regarding the 147-d feeding period the daily body weight gain reached on average 164 g. The overall body weight gain showed a significant improvement by addition of EBP5 at dose levels of 250 or more (250 mg/kg: +2.3%; 500 mg/kg: +3.1%; 1,000 mg/kg: +4.8%; 2,000 mg/kg: +6.6%) in comparison to the control, whereas in turkeys fed diets containing EBP5 at the dose level of 100 mg/kg no significant changes were found (+1.0%) when compared to the control.

Feed Conversion Ratio

The overall feed conversion ratio (feed:gain) of turkeys fed diets without using EBP5 reached 2.138 which indicated a remarkable performance level and outperformed even targets given by the breeder (2.540). Because of the benefits on body weight gain in turkeys fed diets containing EBP5 increased dose levels were associated with significantly decreased overall feed conversion ratios (250 mg/kg: 2.080; 500 mg/kg: 2.050; 1,000 mg/kg: 2.020; 2,000 mg/kg: 2.013) in comparison to the control.

Conclusion

The overall mortality (culling included) amounted to 2.7% indicating an excellent health status of the flock.

The current trial showed a significant improvement in production parameters in birds fed diets containing 250 mg/kg to 2000 mg/kg of the *Bacillus* multi-strain probiotic EBP5.

The body weight gain until d 147 of age was significantly enhanced by EBP5 up to 6.6% (2,000 mg/kg) when compared to the control.

In turkeys fed diets containing the *Bacillus* multi-strain probiotic EBP5 increased dose levels were associated with significantly improved overall feed conversion ratios up to 5.8% (2,000 mg/kg) in comparison to the control.

It is remarkable that at dose levels from 250 mg/kg to 2000 mg/kg the averaged overall dry matter content of excreta was significantly enhanced when compared to the control.

Example 10

Combination of a *Bacillus Composition* with Three *Bacillus* Strains and a Live-Attenuated *Salmonella* Vaccine in Chickens Hundred twenty (120) day-of-hatch Ross x Ross non-sexed broiler chicks were allocated to three different isolation rooms each containing forty (40) broiler chicks at study initiation. Each pen contained approximately four (4) inches of fresh pine shavings, one tube feeder and one bell drinker for ad libitum feeding and drinking.

All birds were coccidia vaccinated at day one and no concomitant drug therapy was used. Pens were checked daily for mortality.

Starter diet (crumbles) and grower diet (pellets) from Day 22 to the end formulations consisted of unmedicated commercial-type broiler. The quantitative composition of the feed was the same for all animals except for the inclusion of the *Bacillus* composition for the treatment group. The *Bacillus* composition comprising DSM32324, DSM25840 and DSM32325 in a ratio of 8:3:5 was mixed at a ratio of $1.6 \times 10^6$ CFU/gram feed into the feed.

AviPro® Megan Vac 1, a live *Salmonella* Typhimurium vaccine produced by Lohmann Animal Health, Maine, USA, in the following termed "Megan Vac", was coarse sprayed at 1 day of age to treatment groups T2 and T3 at one dose per bird in a volume of 0.25 ml per chick.

TABLE 27

| Treatment groups (40 birds in each group) | | |
|---|---|---|
| Group | Megan Vac | *Bacillus* composition in diet |
| T1 | No | No |
| T2 | Yes | No |
| T3 | Yes | $1.6 \times 10^6$ CFU/gram feed |

On Day 3, four ceca and four spleens from each treatment were weighed and collected to confirm vaccine colonization. All remaining birds were orally dosed (gavaged) with $3 \times 10^7$ CFU *Salmonella* Heidelberg (Alali et al., 2013) on Day 4.

On Day 40, just before slaughter, ten birds per treatment were taken from each individual pen, euthanized and ceca's aseptically removed. The ceca samples were tested for *Salmonella*.

Results

The results of *Salmonella* prevalences in ceca and liver/spleen samples collected from four birds on Day 3 (see Table 28) confirm vaccine colonization.

TABLE 28

| *Salmonella* prevalences in ceca and liver/spleen samples | | | |
|---|---|---|---|
| Sample type | Treatment | No | No positive (%) |
| Ceca | T1 | 4 | 0 |
|  | T2 | 4 | 0 |
|  | T3 | 4 | 0 |
| Liver/spleen | T1 | 4 | 0 |
|  | T2 | 4 | 3 |
|  | T3 | 4 | 4 |

Suspect *Salmonella* isolates were confirmed by Poly-O *Salmonella* Specific Antiserum (MiraVista, Indianapolis, Ind.).

Megan Vac alone or with the *Bacillus* composition had numerically lowest number of *Salmonella* in ceca at Day 40 compared to untreated birds (data not shown).

As evident from Table 29 below, FCR of birds fed the Megan Vac+*Bacillus* composition (T3) was lower than in untreated birds (T1) and Megan Vac alone-treated birds (T2).

TABLE 29

| Performance at Day 40 | | | |
|---|---|---|---|
| Treatment | Feed intake (kg/pen) | Weight gain (kg/live bird) | FCR |
| T1 | 95.86 | 1.86 | 1.47 |
| T2 | 110.32 | 2.16 | 1.50 |
| T3 | 106.70 | 2.15 | 1.38 |

Conclusion

The objective was to evaluate the effect of a *Bacillus*-based probiotic on the colonization of a live *Salmonella* Typhimurium vaccine and the *Bacillus* composition's subsequent ability to protect against a *Salmonella* Heidelberg challenge in broiler chicken.

Day 3 samples indicated that the *Bacillus* composition did not affect the vaccine's initial *Salmonella* colonization.

Also, the study indicates that there may be an additive effect to having both the vaccine and the *Bacillus* composition.

REFERENCES

WO2013/153159
WO2016/060934
WO2016/118840
Alali, W. Q, C. L. Hofacre, G. F. Mathis and G. Faltys, 2013. Effect of essential oil compound on shedding and colonization *of Salmonella* enteric serovar heidelberg in broilers, Poultry Science 92: 836-841.
Johnson J, Reid WM. Anticoccidial drugs: lesion scoring techniques in battery and floor-pen experiments with chicken, Exp Parasitol., 1970, Aug;28(1):30-6.
Knap I, Lund B, Kehlet AB, Hofacre C, Mathis G.: *Bacillus* licheniformis prevents necrotic enteritis in broiler chicken. Avian Dis. 2010 Jun;54(2):931-5.
Timbermont L, et al. Lanckriet A, Gholamiandehkordi AR, Pasmans F, Martel A, Haesebrouck F, Ducatelle R, Van Immerseel F., Origin of Clostridium perfringens isolates determines the ability to induce necrotic enteritis in broilers., Comp Immunol Microbiol Infect Dis., 2009, Nov;32(6):503-12
Waititu et al. Effect of Supplementing Direct-Fed Microbials on Broiler Performance, Nutrient Digestibilities, and Immune Responses. Poult Sci, 2014, 93 (3), 625-635
Wang et al., Comparison of gyrB gene sequences, 16S rRNA gene sequences and DNA-DNA hybridization in the *Bacillus subtilis* group, Int J Syst Evol Microbiol. 2007 Aug;57(Pt 8):1846-50.
Guidance on the assessment of bacterial susceptibility to inhibitorys of human and veterinary importance", EFSA Journal 2012;10(6):2740

The invention claimed is:

1. A method comprising administering to an animal the *Bacillus amyloliquefaciens* strain deposited at DSMZ under accession number DSM25840, the *Bacillus subtilis* strain deposited at DSMZ under accession number DSM32324, and the *Bacillus subtilis* strain deposited at DSMZ under accession number DSM32325.

2. The method of claim 1, wherein the animal is selected from poultry, horses, ruminants, swine, rodents, fish, and crustaceans.

3. The method of claim 1, wherein the animal is a poultry animal.

4. The method of claim 1, wherein the *Bacillus* strains are administered to the animal in amounts effective to inhibit growth of *Escherichia coli* and/or *Clostridium perfringens*.

5. The method of claim 1, wherein the *Bacillus* strains are administered to the animal in amounts effective to improve one or more animal performance parameters selected from weight gain (WG), feed conversion ratio (FCR), necrotic enteritis lesion scoring, necrotic enteritis frequency, necrotic enteritis mortality, European Production Efficacy Factor (EPEF), and mortality.

6. The method of claim 1, wherein the *Bacillus* strains are administered to the animal in amounts effective to improve digestibility of an animal feed fed to the animal.

7. An animal feed additive comprising the *Bacillus subtilis* strain deposited at DSMZ under accession number DSM32324, the *Bacillus amyloliquefaciens* strain deposited at DSMZ under accession number DSM25840, and the *Bacillus subtilis* strain deposited at DSMZ under accession number DSM32325 in a DSM32324: DSM25840: DSM32325 ratio of about 8:3:5.

8. The animal feed additive of claim 7, comprising at least $5 \times 10^4$ CFU of DSM32324, at least $5 \times 10^4$ CFU of DSM25480, and at least $5 \times 10^4$ CFU of DSM32325 per gram of said animal feed additive.

9. A pelleted animal feed comprising the *Bacillus subtilis* strain deposited at DSMZ under accession number DSM32324, the *Bacillus amyloliquefaciens* strain deposited at DSMZ under accession number DSM25840, and the *Bacillus subtilis* strain deposited at DSMZ under accession number DSM32325 in a DSM32324: DSM25840: DSM32325 ratio of about 8:3:5.

10. The method of claim 1, wherein the *Bacillus* strains are administered to the animal in a composition comprising at least $5 \times 10^4$ colony forming units (CFU) of each of the *Bacillus* strains per gram of composition.

11. The method of claim 1, wherein the *Bacillus* strains are administered to the animal in a composition comprising the *Bacillus* strains in a DSM32324: DSM25840: DSM32325 ratio of about 8:3:5.

12. The method of claim 1, wherein the *Bacillus* strains are administered to the animal in a composition comprising about $1 \times 10^5$ to about $1 \times 10^{12}$ colony forming units (CFU) of the *Bacillus* strains per gram of composition.

13. The method of claim 1, wherein the *Bacillus* strains are administered to the animal as spores.

14. The method of claim 1, wherein the *Bacillus* strains are administered to the animal in a liquid formulation.

15. The method of claim 1, wherein the *Bacillus* strains are administered to the animal in a solid formulation.

16. The method of claim 1, wherein the *Bacillus* strains are administered to the animal as part of a composition comprising one or more vitamins, minerals, vegetable proteins, forages, milks and/or milk replacements.

17. The method of claim 1, wherein the animal is monogastric.

18. The method of claim 1, wherein the animal is a swine.

19. The method of claim 1, wherein the animal is a ruminant animal.

20. The method of claim 1, wherein the animal is a cattle.

* * * * *